(12) United States Patent
Ton et al.

(10) Patent No.: US 7,651,521 B2
(45) Date of Patent: *Jan. 26, 2010

(54) COREWIRE ACTUATED DELIVERY SYSTEM WITH FIXED DISTAL STENT-CARRYING EXTENSION

(75) Inventors: Dai T. Ton, Milpitas, CA (US); Julian Nikolchev, Portola Valley, CA (US); Nicholas C. Debeer, Montara, CA (US); William R. George, Santa Cruz, CA (US)

(73) Assignee: CardioMind, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/991,721

(22) Filed: Nov. 18, 2004

(65) Prior Publication Data
US 2005/0209675 A1    Sep. 22, 2005

Related U.S. Application Data

(63) Continuation-in-part of application No. 10/792,679, filed on Mar. 2, 2004.

(51) Int. Cl.
*A61F 2/84* (2006.01)
(52) U.S. Cl. .................. 623/1.12; 623/1.11
(58) Field of Classification Search ........... 623/1.11, 623/1.12, 1.23; 606/108, 191, 192, 194, 606/198
See application file for complete search history.

(56) References Cited

U.S. PATENT DOCUMENTS

| 4,503,569 A | 3/1985 | Dotter |
| 4,512,338 A | 4/1985 | Balko et al. |
| 4,553,545 A | 11/1985 | Maass et al. |
| 4,562,596 A | 1/1986 | Kornberg |
| 4,580,568 A | 4/1986 | Gianturco |
| 4,655,771 A | 4/1987 | Wallsten |
| 4,665,918 A | 5/1987 | Garza et al. |
| 4,732,152 A | 3/1988 | Wallsten et al. |
| 4,733,665 A | 3/1988 | Palmaz |

(Continued)

FOREIGN PATENT DOCUMENTS

DE          4420142         9/1994

(Continued)

OTHER PUBLICATIONS

The Random House College Dictionary, Random House Inc (1980) New York, pp. 7 and 1510.*

(Continued)

*Primary Examiner*—Anhtuan T Nguyen
*Assistant Examiner*—Amy T Lang
(74) *Attorney, Agent, or Firm*—Townsend and Townsend and Crew LLP

(57) ABSTRACT

Medical device and methods for delivery or implantation of prostheses within hollow body organs and vessels or other luminal anatomy are disclosed. The subject technologies may be used in the treatment of atherosclerosis in stenting procedures. For such purposes, a self-expanding stent is deployed in connection with an angioplasty procedure with a corewire actuated delivery system having a fixed distal stent-carrying extension. Withdrawal of the corewire retracts a restraint freeing the stent from a collapsed state, whereupon the stent assumes an expanded configuration set in apposition to the interior surface of a vessel lumen in order to help maintain the vessel open.

21 Claims, 16 Drawing Sheets

U.S. PATENT DOCUMENTS

| | | |
|---|---|---|
| 4,762,128 A | 8/1988 | Rosenbluth |
| 4,768,507 A | 9/1988 | Fischell et al. |
| 4,771,773 A | 9/1988 | Kropf |
| 4,776,337 A | 10/1988 | Palmaz |
| 4,830,003 A | 5/1989 | Wolff et al. |
| 4,848,343 A | 7/1989 | Wallsten et al. |
| 4,875,480 A | 10/1989 | Imbert |
| 4,878,906 A | 11/1989 | Lindemann et al. |
| 4,893,623 A | 1/1990 | Rosenbluth |
| 4,913,141 A | 4/1990 | Hillstead |
| 4,950,227 A | 8/1990 | Savin et al. |
| 4,954,126 A | 9/1990 | Wallsten |
| 4,969,890 A | 11/1990 | Sugita et al. |
| 4,990,151 A | 2/1991 | Wallsten |
| 4,990,155 A | 2/1991 | Wilkoff |
| 4,998,539 A | 3/1991 | Delsanti |
| 5,019,085 A | 5/1991 | Hillstead |
| 5,019,090 A | 5/1991 | Pinchuk |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,067,957 A | 11/1991 | Jervis |
| 5,071,407 A | 12/1991 | Termin et al. |
| 5,089,006 A | 2/1992 | Stiles |
| 5,092,877 A | 3/1992 | Pinchuk |
| 5,102,417 A | 4/1992 | Palmaz |
| 5,108,407 A | 4/1992 | Geremia et al. |
| 5,108,416 A | 4/1992 | Ryan et al. |
| 5,122,136 A | 6/1992 | Guglielmi et al. |
| 5,147,370 A | 9/1992 | McNamara et al. |
| 5,158,548 A | 10/1992 | Lau et al. |
| 5,180,367 A | 1/1993 | Kontos et al. |
| 5,192,297 A | 3/1993 | Hull |
| 5,201,757 A | 4/1993 | Heyn et al. |
| 5,221,261 A | 6/1993 | Termin et al. |
| 5,242,399 A | 9/1993 | Lau et al. |
| 5,242,452 A | 9/1993 | Inoue |
| 5,246,445 A | 9/1993 | Yachia et al. |
| 5,263,964 A | 11/1993 | Purdy |
| 5,266,073 A | 11/1993 | Wall |
| 5,290,305 A | 3/1994 | Inoue |
| 5,306,294 A | 4/1994 | Winston et al. |
| 5,320,635 A * | 6/1994 | Smith ..................... 606/180 |
| 5,334,210 A | 8/1994 | Gianturco |
| 5,354,295 A | 10/1994 | Guglielmi et al. |
| 5,360,401 A | 11/1994 | Turnland |
| 5,372,600 A | 12/1994 | Beyar et al. |
| 5,382,259 A | 1/1995 | Phelps et al. |
| 5,407,432 A | 4/1995 | Solar |
| 5,415,664 A | 5/1995 | Pinchuk |
| 5,423,829 A | 6/1995 | Pham et al. |
| 5,433,723 A | 7/1995 | Lindenberg et al. |
| 5,443,477 A | 8/1995 | Marin et al. |
| 5,445,646 A | 8/1995 | Euteneuer et al. |
| 5,476,505 A | 12/1995 | Limon |
| 5,484,444 A | 1/1996 | Braunschweiler et al. |
| 5,486,195 A | 1/1996 | Myers et al. |
| 5,507,771 A | 4/1996 | Gianturco |
| 5,522,836 A | 6/1996 | Palermo |
| 5,522,883 A | 6/1996 | Slater et al. |
| 5,534,007 A | 7/1996 | St. Germain et al. |
| 5,540,680 A | 7/1996 | Guglielmi et al. |
| 5,554,181 A | 9/1996 | Das |
| 5,569,245 A | 10/1996 | Guglielmi et al. |
| 5,571,135 A | 11/1996 | Fraser et al. |
| 5,578,074 A | 11/1996 | Mirigian |
| 5,591,196 A | 1/1997 | Marin et al. |
| 5,601,600 A | 2/1997 | Ton |
| 5,618,300 A | 4/1997 | Marin et al. |
| 5,643,254 A | 7/1997 | Scheldrup et al. |
| 5,653,748 A | 8/1997 | Strecker |
| 5,683,451 A | 11/1997 | Lenker et al. |
| 5,690,643 A | 11/1997 | Wijay |
| 5,690,644 A | 11/1997 | Yurek et al. |
| 5,702,364 A | 12/1997 | Euteneuer et al. |
| 5,702,418 A | 12/1997 | Ravenscroft |
| 5,725,551 A | 3/1998 | Myers et al. |
| 5,733,267 A | 3/1998 | Del Toro |
| 5,733,325 A | 3/1998 | Robinson et al. |
| 5,772,609 A | 6/1998 | Nguyen et al. |
| 5,772,668 A | 6/1998 | Summers et al. |
| 5,772,669 A | 6/1998 | Vrba |
| 5,776,141 A | 7/1998 | Klein et al. |
| 5,776,142 A | 7/1998 | Gunderson |
| 5,782,838 A | 7/1998 | Beyar et al. |
| 5,788,707 A | 8/1998 | Del Toro et al. |
| 5,797,857 A | 8/1998 | Obitsu |
| 5,797,952 A | 8/1998 | Klein |
| 5,800,455 A | 9/1998 | Palermo et al. |
| 5,800,517 A | 9/1998 | Anderson et al. |
| 5,807,398 A | 9/1998 | Shaknovich |
| 5,810,837 A | 9/1998 | Hofmann et al. |
| 5,817,101 A | 10/1998 | Fiedler |
| 5,824,041 A | 10/1998 | Lenker et al. |
| 5,824,058 A | 10/1998 | Ravenscroft et al. |
| 5,843,090 A | 12/1998 | Schuetz |
| 5,851,206 A | 12/1998 | Guglielmi et al. |
| 5,855,578 A | 1/1999 | Guglielmi et al. |
| 5,873,907 A | 2/1999 | Frantzen |
| 5,891,128 A | 4/1999 | Gia et al. |
| 5,919,187 A | 7/1999 | Guglielmi et al. |
| 5,919,204 A | 7/1999 | Lukic et al. |
| 5,919,225 A | 7/1999 | Lau et al. |
| 5,920,975 A | 7/1999 | Morales |
| 5,941,888 A | 8/1999 | Wallace et al. |
| 5,944,726 A | 8/1999 | Blaeser et al. |
| 5,957,930 A | 9/1999 | Vrba |
| 5,968,052 A | 10/1999 | Sullivan, III et al. |
| 5,980,485 A | 11/1999 | Grantz et al. |
| 5,980,514 A | 11/1999 | Kupiecki et al. |
| 5,980,530 A | 11/1999 | Willard et al. |
| 5,984,929 A | 11/1999 | Bashiri et al. |
| 5,989,242 A | 11/1999 | Saadat et al. |
| 5,989,280 A | 11/1999 | Euteneuer et al. |
| 6,004,328 A | 12/1999 | Solar |
| 6,015,429 A | 1/2000 | Lau et al. |
| 6,019,737 A | 2/2000 | Murata |
| 6,019,779 A | 2/2000 | Thorud et al. |
| 6,027,516 A | 2/2000 | Kolobow et al. |
| 6,027,520 A | 2/2000 | Tsugita et al. |
| 6,042,588 A | 3/2000 | Munsinger et al. |
| 6,042,589 A | 3/2000 | Marianne |
| 6,042,605 A | 3/2000 | Martin et al. |
| 6,048,360 A | 4/2000 | Khosravi et al. |
| 6,056,759 A | 5/2000 | Fiedler |
| 6,059,779 A | 5/2000 | Mills |
| 6,059,813 A | 5/2000 | Vrba et al. |
| 6,063,101 A | 5/2000 | Jacobsen et al. |
| 6,063,104 A | 5/2000 | Villar et al. |
| 6,068,634 A | 5/2000 | Lorentzen Cornelius et al. |
| 6,068,644 A | 5/2000 | Lulo et al. |
| 6,071,286 A | 6/2000 | Mawad |
| 6,077,297 A | 6/2000 | Robinson et al. |
| 6,093,194 A | 7/2000 | Mikus et al. |
| 6,096,034 A | 8/2000 | Kupiecki et al. |
| 6,096,045 A | 8/2000 | Del Toro et al. |
| 6,102,942 A | 8/2000 | Ahari |
| 6,113,608 A | 9/2000 | Monroe et al. |
| 6,117,140 A | 9/2000 | Munsinger |
| 6,120,522 A | 9/2000 | Vrba et al. |
| 6,123,714 A | 9/2000 | Gia et al. |
| 6,123,720 A | 9/2000 | Anderson et al. |
| 6,126,685 A | 10/2000 | Lenker et al. |

| | | | | | | |
|---|---|---|---|---|---|---|
| 6,139,524 | A | 10/2000 | Killion | 6,517,569 B2 | 2/2003 | Mikus et al. |
| 6,139,564 | A | 10/2000 | Teoh | 6,520,986 B2 | 2/2003 | Martin et al. |
| 6,156,061 | A | 12/2000 | Wallace et al. | 6,530,947 B1 | 3/2003 | Euteneuer et al. |
| 6,161,029 | A | 12/2000 | Spreigl et al. | 6,533,805 B1 | 3/2003 | Jervis |
| 6,165,178 | A | 12/2000 | Bashiri et al. | 6,533,807 B2 | 3/2003 | Wolinsky et al. |
| 6,168,592 | B1 | 1/2001 | Kupiecki et al. | 6,537,295 B2 | 3/2003 | Petersen |
| 6,168,616 | B1 | 1/2001 | Brown, III | 6,558,415 B2 | 5/2003 | Thompson |
| 6,168,618 | B1 | 1/2001 | Frantzen | 6,562,063 B1 | 5/2003 | Euteneuer et al. |
| 6,174,327 | B1 | 1/2001 | Mertens et al. | 6,562,064 B1 | 5/2003 | deBeer |
| 6,183,481 | B1 | 2/2001 | Lee et al. | 6,579,297 B2 | 6/2003 | Bicek et al. |
| 6,183,505 | B1 | 2/2001 | Mohn, Jr. et al. | 6,579,308 B1 | 6/2003 | Jansen et al. |
| 6,193,708 | B1 | 2/2001 | Ken et al. | 6,582,460 B1 | 6/2003 | Cryer |
| 6,200,305 | B1 | 3/2001 | Berthiaume et al. | 6,602,226 B1 | 8/2003 | Smith et al. |
| 6,203,550 | B1 | 3/2001 | Olson | 6,602,272 B2 | 8/2003 | Boylan et al. |
| 6,206,888 | B1 | 3/2001 | Bicek et al. | 6,607,539 B1 | 8/2003 | Hayashi et al. |
| 6,214,036 | B1 | 4/2001 | Letendre et al. | 6,607,551 B1 | 8/2003 | Sullivan et al. |
| 6,221,081 | B1 | 4/2001 | Mikus et al. | 6,613,079 B1 | 9/2003 | Wolinsky et al. |
| 6,228,110 | B1 | 5/2001 | Munsinger | 6,620,152 B2 | 9/2003 | Guglielmi |
| 6,238,430 | B1 | 5/2001 | Klumb et al. | 6,623,518 B2 | 9/2003 | Thompson et al. |
| 6,241,758 | B1 | 6/2001 | Cox | 6,626,938 B1 | 9/2003 | Butaric et al. |
| 6,245,097 | B1 | 6/2001 | Inoue | 6,629,981 B2 | 10/2003 | Bui et al. |
| 6,248,122 | B1 | 6/2001 | Klumb et al. | 6,645,237 B2 | 11/2003 | Klumb et al. |
| 6,254,609 | B1 | 7/2001 | Vrba et al. | 6,645,238 B2 | 11/2003 | Smith |
| 6,254,611 | B1 | 7/2001 | Vrba | 6,656,212 B2 | 12/2003 | Ravenscroft et al. |
| 6,254,628 | B1 | 7/2001 | Wallace et al. | 6,660,031 B2 | 12/2003 | Tran et al. |
| 6,264,683 | B1 | 7/2001 | Stack et al. | 6,660,032 B2 | 12/2003 | Klumb et al. |
| 6,267,783 | B1 | 7/2001 | Letendre et al. | 6,663,660 B2 | 12/2003 | Dusbabek et al. |
| 6,270,504 | B1 | 8/2001 | Lorentzen Cornelius et al. | 6,666,881 B1 | 12/2003 | Richter et al. |
| 6,273,881 | B1 | 8/2001 | Kiemeneij | 6,669,719 B2 | 12/2003 | Wallace et al. |
| 6,280,465 | B1 | 8/2001 | Cryer | 6,676,666 B2 | 1/2004 | Vrba et al. |
| 6,287,331 | B1 | 9/2001 | Heath | 6,679,910 B1 | 1/2004 | Granada |
| 6,302,893 | B1 | 10/2001 | Limon et al. | 6,689,120 B1 | 2/2004 | Gerdts |
| 6,306,141 | B1 | 10/2001 | Jervis | 6,692,521 B2 | 2/2004 | Pinchasik |
| 6,342,066 | B1 | 1/2002 | Toro et al. | 6,699,274 B2 | 3/2004 | Stinson |
| 6,344,041 | B1 | 2/2002 | Kupiecki et al. | 6,702,843 B1 | 3/2004 | Brown et al. |
| 6,346,118 | B1 | 2/2002 | Baker et al. | 6,709,425 B2 | 3/2004 | Gambale et al. |
| 6,350,277 | B1 | 2/2002 | Kocur | 6,716,238 B2 | 4/2004 | Elliott |
| 6,350,278 | B1 | 2/2002 | Lenker et al. | 6,726,714 B2 | 4/2004 | DiCaprio et al. |
| 6,361,637 | B2 | 3/2002 | Martin et al. | 6,733,519 B2 | 5/2004 | Lashinski et al. |
| 6,368,344 | B1 | 4/2002 | Fitz | 6,736,839 B2 | 5/2004 | Cummings |
| 6,371,962 | B1 | 4/2002 | Ellis et al. | 6,802,858 B2 | 10/2004 | Gambale et al. |
| 6,375,660 | B1 | 4/2002 | Fischell et al. | 6,814,746 B2 | 11/2004 | Thompson et al. |
| 6,379,365 | B1 | 4/2002 | Diaz | 6,818,014 B2 | 11/2004 | Brown et al. |
| 6,380,457 | B1 | 4/2002 | Yurek et al. | 6,830,575 B2 | 12/2004 | Stenzel et al. |
| 6,383,174 | B1 | 5/2002 | Eder | 6,833,003 B2 * | 12/2004 | Jones et al. ............... 623/1.11 |
| 6,387,118 | B1 | 5/2002 | Hanson | 6,858,034 B1 | 2/2005 | Hijlkema et al. |
| 6,391,050 | B1 | 5/2002 | Broome | 6,860,899 B1 | 3/2005 | Rivelli, Jr. |
| 6,391,051 | B2 | 5/2002 | Sullivan, III et al. | 6,936,058 B2 | 8/2005 | Forde et al. |
| 6,395,017 | B1 | 5/2002 | Dwyer et al. | 6,936,065 B2 | 8/2005 | Khan et al. |
| 6,409,750 | B1 | 6/2002 | Hyodoh et al. | 6,989,024 B2 | 1/2006 | Hebert et al. |
| 6,409,752 | B1 | 6/2002 | Boatman et al. | 7,011,673 B2 | 3/2006 | Fischell et al. |
| 6,413,269 | B1 | 7/2002 | Bui et al. | 7,074,236 B2 | 7/2006 | Rabkin et al. |
| 6,416,536 | B1 | 7/2002 | Yee | 7,172,620 B2 | 2/2007 | Gilson |
| 6,416,545 | B1 | 7/2002 | Mikus et al. | 7,300,460 B2 | 11/2007 | Levine et al. |
| 6,423,090 | B1 | 7/2002 | Hancock | 2001/0034548 A1 | 10/2001 | Vrba et al. |
| 6,425,898 | B1 | 7/2002 | Wilson et al. | 2001/0047185 A1 | 11/2001 | Satz |
| 6,425,914 | B1 | 7/2002 | Wallace et al. | 2001/0049547 A1 | 12/2001 | Moore |
| 6,425,915 | B1 | 7/2002 | Khosravi et al. | 2001/0049550 A1 | 12/2001 | Martin et al. |
| 6,428,489 | B1 | 8/2002 | Jacobsen et al. | 2002/0002397 A1 | 1/2002 | Martin et al. |
| 6,428,566 | B1 | 8/2002 | Holt | 2002/0032431 A1 | 3/2002 | Kiemeneij |
| 6,432,080 | B2 | 8/2002 | Pederson, Jr. et al. | 2002/0035393 A1 | 3/2002 | Lashinski et al. |
| 6,432,129 | B2 | 8/2002 | DiCaprio | 2002/0040236 A1 | 4/2002 | Lau et al. |
| 6,447,540 | B1 | 9/2002 | Fontaine et al. | 2002/0045928 A1 | 4/2002 | Boekstegers |
| 6,448,700 | B1 | 9/2002 | Gupta et al. | 2002/0045930 A1 | 4/2002 | Burg et al. |
| 6,451,025 | B1 | 9/2002 | Jervis | 2002/0049490 A1 | 4/2002 | Pollock et al. |
| 6,454,795 | B1 | 9/2002 | Chuter | 2002/0068966 A1 | 6/2002 | Holman et al. |
| 6,458,092 | B1 | 10/2002 | Gambale et al. | 2002/0072729 A1 | 6/2002 | Hoste et al. |
| 6,468,266 | B1 | 10/2002 | Bashiri et al. | 2002/0095147 A1 | 7/2002 | Shadduck |
| 6,468,301 | B1 | 10/2002 | Amplatz et al. | 2002/0095168 A1 | 7/2002 | Griego et al. |
| 6,482,227 | B1 | 11/2002 | Solovay | 2002/0099433 A1 | 7/2002 | Fischell et al. |
| 6,485,515 | B2 | 11/2002 | Strecker | 2002/0120322 A1 | 8/2002 | Thompson et al. |
| 6,488,700 | B2 | 12/2002 | Klumb et al. | 2002/0120323 A1 | 8/2002 | Thompson et al. |
| 6,517,548 | B2 | 2/2003 | Lorentzen Cornelius et al. | 2002/0120324 A1 | 8/2002 | Holman et al. |

| | | |
|---|---|---|
| 2002/0138129 A1 | 9/2002 | Armstrong et al. |
| 2002/0147491 A1 | 10/2002 | Khan et al. |
| 2002/0161342 A1 | 10/2002 | Rivelli, Jr. et al. |
| 2002/0169494 A1 | 11/2002 | Mertens et al. |
| 2002/0188341 A1 | 12/2002 | Elliott et al. |
| 2003/0014103 A1 | 1/2003 | Inoue |
| 2003/0018319 A1 | 1/2003 | Kiemeneij |
| 2003/0036768 A1 | 2/2003 | Hutchins et al. |
| 2003/0040771 A1 | 2/2003 | Hyodoh et al. |
| 2003/0040772 A1 | 2/2003 | Hyodoh et al. |
| 2003/0055377 A1 | 3/2003 | Sirhan et al. |
| 2003/0065375 A1 | 4/2003 | Eskuri |
| 2003/0069521 A1 | 4/2003 | Reynolds et al. |
| 2003/0105508 A1 | 6/2003 | Johnson et al. |
| 2003/0135266 A1 | 7/2003 | Chew et al. |
| 2003/0149467 A1* | 8/2003 | Linder et al. ............... 623/1.11 |
| 2003/0163156 A1 | 8/2003 | Hebert et al. |
| 2003/0163189 A1 | 8/2003 | Thompson et al. |
| 2004/0010265 A1 | 1/2004 | Karpiel |
| 2004/0049547 A1 | 3/2004 | Matthews et al. |
| 2004/0093063 A1* | 5/2004 | Wright et al. ............... 623/1.12 |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0220585 A1 | 11/2004 | Nikolchev |
| 2004/0260377 A1 | 12/2004 | Flomenblit et al. |
| 2005/0080430 A1 | 4/2005 | Wright, Jr. et al. |
| 2005/0096724 A1 | 5/2005 | Stenzel et al. |
| 2005/0209670 A1* | 9/2005 | George et al. ............... 623/1.11 |
| 2005/0209671 A1* | 9/2005 | Ton et al. .................... 623/1.11 |
| 2005/0209672 A1 | 9/2005 | George |
| 2006/0111771 A1 | 5/2006 | Ton et al. |
| 2006/0136037 A1 | 6/2006 | DeBeer et al. |
| 2006/0247661 A1 | 11/2006 | Richards et al. |
| 2006/0270948 A1 | 11/2006 | Viswanathan et al. |
| 2006/0271097 A1 | 11/2006 | Ramzipoor et al. |
| 2006/0276886 A1 | 12/2006 | George et al. |
| 2007/0027522 A1 | 2/2007 | Chang et al. |
| 2007/0043419 A1 | 2/2007 | Nikolchev et al. |
| 2007/0073379 A1 | 3/2007 | Chang et al. |
| 2007/0100414 A1 | 5/2007 | Licata et al. |
| 2007/0100415 A1 | 5/2007 | Licata |
| 2007/0100416 A1 | 5/2007 | Licata |
| 2007/0100417 A1 | 5/2007 | Licata |
| 2007/0100418 A1 | 5/2007 | Licata |
| 2008/0015541 A1* | 1/2008 | Rosenbluth et al. .......... 604/509 |
| 2008/0071309 A1* | 3/2008 | Mazzocchi et al. .......... 606/200 |
| 2008/0221666 A1 | 9/2008 | Licata et al. |

FOREIGN PATENT DOCUMENTS

| | | |
|---|---|---|
| EP | 0667 132 | 8/1995 |
| EP | 0747021 | 11/1996 |
| EP | 1 157 673 | 11/2001 |
| EP | 1518515 | 3/2005 |
| WO | WO 98/23241 | 6/1998 |
| WO | WO 99/04728 | 2/1999 |
| WO | WO 00/18330 | 4/2000 |
| WO | WO 01/78627 | 10/2001 |
| WO | WO 03/073963 | 9/2003 |
| WO | WO 2004/087006 | 10/2004 |
| WO | WO 2005/092241 | 10/2005 |
| WO | WO 2005/094727 | 10/2005 |

OTHER PUBLICATIONS

Kandzari, et al. "Clinical and Angiographic Efficacy of a Self-Expanding Nitinol Stent in Saphenous Vein Graft Athersclerotic Disease" Am. Heart J 145(5):868-874 (2003).

Welt, et al. "Coronary Artery Stents: Design and Biologic Considerations" Cardiology Special Edition 9(2) 9-14(2003).

Schuessler et al., Stent Materials and Manufacturing: Requirements and Possibilities/Opportunities, ASM Materials & Processes, Anaheim, CA. (Sep. 8-10, 2003).

Fischell, M.D. FACC, Tim A., "A Fixed Guidewire Stent Delivery System Rationale and Design" TCT, Washington, D.C. (Sep. 24, 2002).

Poncet, Phillippe P., "Nitinol Medical Device Design Considerations" MEMRY Corporation, 4065 Campbell Avenue, Menlo Park, California 94025, pp. 1-12.

Rieu et al., "Radial Force of Coronary Stents: A Comparative Analysis"*Catheterization and Cardiovascular Interventions* 46:380-391 (1999).

Bonsignore, Craig, "A Decade of Evolution in Stent Design" Cordis Corporation Nitinol Devices & Components. 47533 Westinghouse Drive, Fremont. California 94539 (2002).

Duerig et al., "An overview of superelastic stent design" Min fnvas Ther & Affied Technol. 9(3/4 ):235-246 (2000).

Stoeckel et al., "A Survey of Stent Designs" Min lnvas Ther & Allied Technol 11(4):137-147 (2002).

Rogers, C. "DES Overview: Agents: release mechanism and stent platform", PowerPoint Presentation, 51 pages total.

* cited by examiner

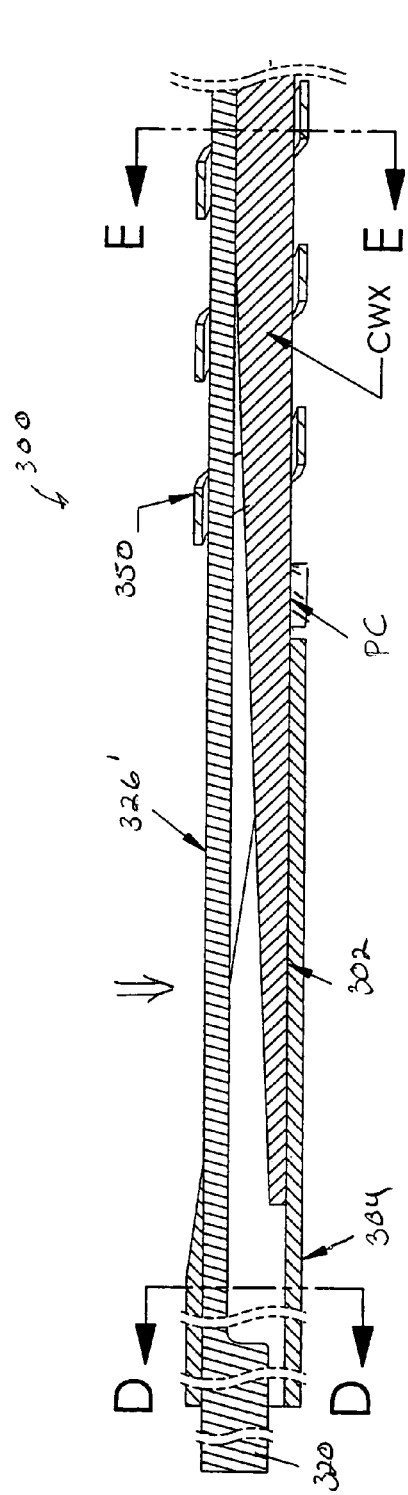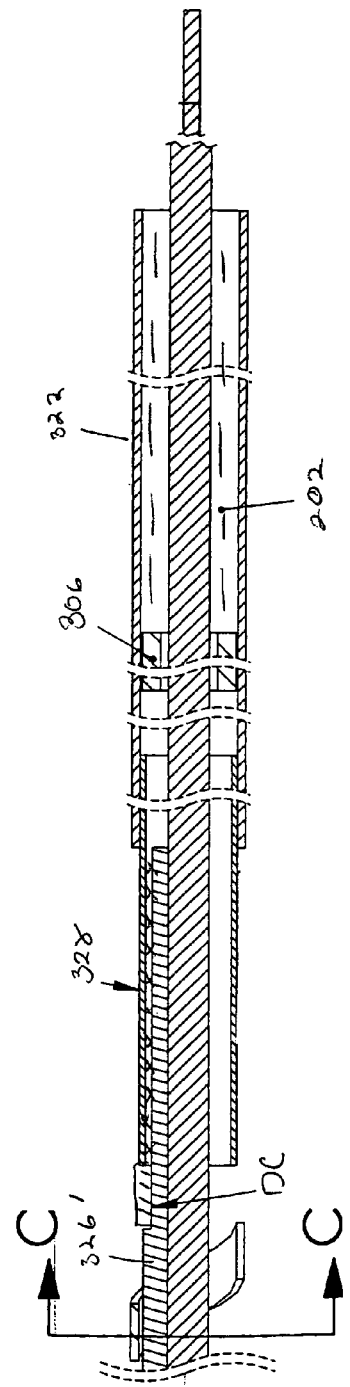
Fig. 11A
Fig. 11B

SECTION C-C

SECTION D-D

SECTION E-E

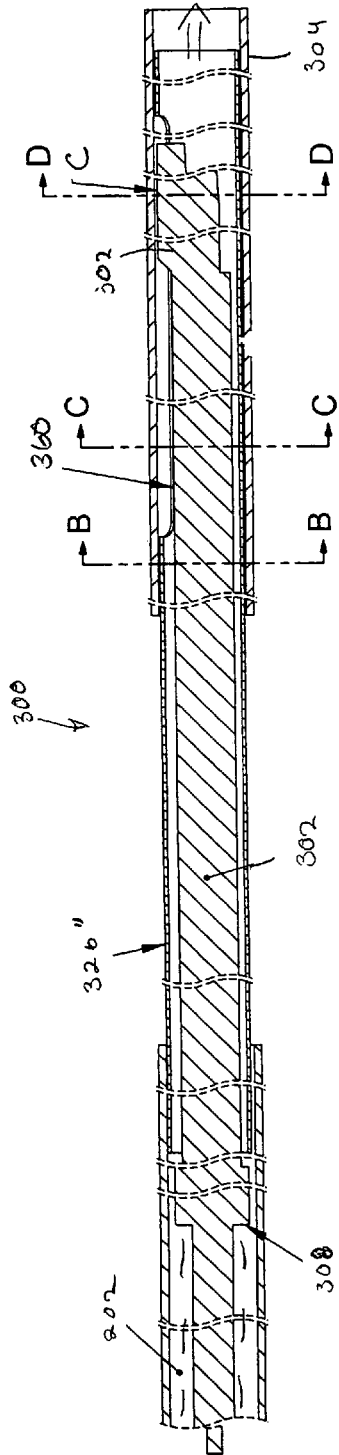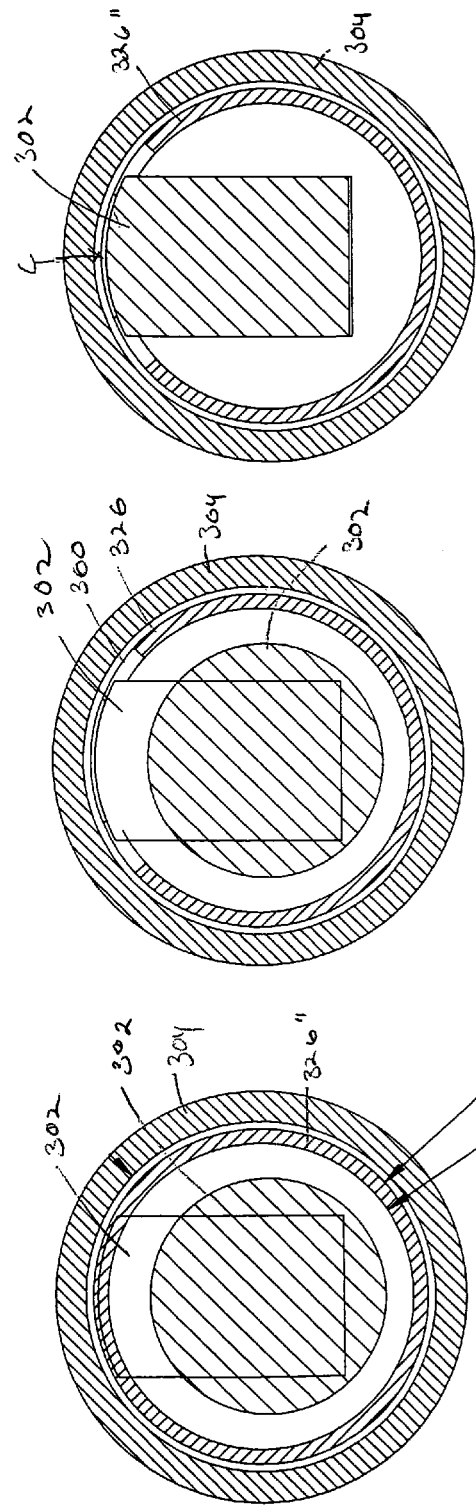

SECTION C-C

SECTION B-B

COREWIRE ACTUATED DELIVERY SYSTEM WITH FIXED DISTAL STENT-CARRYING EXTENSION

CROSS-REFERENCE TO RELATED APPLICATIONS

This is a Continuation-In-Part of co-pending U.S. patent application Ser. No. 10/792,679 filed Mar. 2, 2004, which application is incorporated by reference herein in its entirety.

FIELD OF THE INVENTION

The present invention relates generally to medical device and methods. More particularly, it relates to delivery systems for implanting prostheses within hollow body organs and vessels or other luminal anatomy.

BACKGROUND OF THE INVENTION

Implants such as stents and occlusive coils have been used in patients for a wide variety of reasons. One of the most common "stenting" procedures is carried out in connection with the treatment of atherosclerosis, a disease which results in a narrowing and stenosis of body lumens, such as the coronary arteries. At the site of the narrowing (i.e., the site of a lesion) a balloon is typically dilatated in an angioplasty procedure to open the vessel. A stent is set in apposition to the interior surface of the lumen in order to help maintain an open passageway. This result may be effected by means of scaffolding support alone or by virtue of the presence of one or more drugs carried by the stent aiding in the prevention of restenosis.

Various stent designs have been developed and used clinically, but self-expandable and balloon-expandable stent systems and their related deployment techniques are now predominant. Examples of self-expandable stents currently in use are the Magic WALLSTENT® stents and Radius stents (Boston Scientific). A commonly used balloon-expandable stent is the Cypher® stent (Cordis Corporation). Additional self-expanding stent background is presented in: "An Overview of Superelastic Stent Design," Min. Invas Ther & Allied Technol 2002: 9(3/4) 235-246, "A Survey of Stent Designs," Min. Invas Ther & Allied Technol 2002: 11(4) 137-147, and "Coronary Artery Stents: Design and Biologic Considerations," Cardiology Special Edition, 2003: 9(2) 9-14, "Clinical and Angiographic Efficacy of a Self-Expanding Stent" Am Heart J 2003: 145(5) 868-874.

Because self-expanding prosthetic devices need not be set over a balloon (as with balloon-expandable designs), self-expanding stent delivery systems can be designed to a relatively smaller outer diameter than their balloon-expandable counterparts. As such, self-expanding stents may be better suited to reach the smallest vasculature or achieve access in more difficult cases.

To realize such benefits, however, there continues to be a need in developing improved delivery systems. Problems encountered with known systems include drawbacks ranging from failure to provide means to enable precise placement of the subject prosthetic, to a lack of space efficiency in delivery system design. Poor placement hampers stent efficacy. Space inefficiency in system design prohibits scaling the systems to sizes as small as necessary to enable difficult access or small-vessel procedures (i.e., in tortuous vasculature or vessels having a diameter less than 3 mm, even less than 2 mm).

One known stent delivery system comprises a simple sheath set over a pusher in abutment with a stent. An example of such a system is disclosed in U.S. Pat. No. 4,580,568. Though elegant in design, the system fails to offer desired functional characteristics. Particularly, such a system is prone to misuse when a physician who in not intimately familiar with the hardware retracts or pushes the wrong one of the stent-abutting member or the sheath in an effort to free the stent. Dedicated handle systems have been developed to address this problem. Examples are provide in WO 99/04728, WO 00/18330, WO 98/23241, EP-A-747021, DE-A-44 20142 and U.S. Pat. No. 5,433,723.

Even when not misused, simple sheath system present issues with precise stent placement stemming from the fact that the sheath cannot be locked-down at the proximal end of an access catheter (e.g., at a hemostatic valve) while deploying the stent. As a result, it is difficult to prevent inadvertent axial movement of the stent. Because the sheath cannot be held onto, stent deployment requires that a user hold the pusher member (or handle attached thereto) steady while withdrawing the sheath in order to avoid pushing the stent forward within the vessel thereby complicating stent placement or producing "skid-marks" and even vessel perforation.

The system described in U.S. Pat. No. 5,534,007 assigned to SciMed Life Systems, Inc. offers an alternative to a simple-sheath type system for deploying self-expandable stents. The proximal end of the noted system can be locked-down to possibly aid in reducing stent movement during restraint withdrawal. Yet, the system requires a collapsible, bellows-type sheath portioned between the stationary proximal sleeve and the moveable distal restraint. Furthermore, the system is deployed over a guidewire. Because of the large "over-the-guidewire size" and increasing size of the device resulting by compression of the bellows, the device is not believed capable of being able to access or be withdrawn from the smallest and/or most tortuous anatomy.

Accordingly, there exists a need for a system to better enable precise stent placement than a simple sheath system, but offering improved space efficiency over other known self-expanding stent delivery systems such as that in the '007 patent. Those with skill in the art may also appreciate further advantages or benefits of the invention.

SUMMARY OF THE INVENTION

The present invention offers a highly-advantageous system for precise stent placement, allowing a user to conveniently lock-down the system if desired and deliver a stent thus set in place. The system includes a stent and a delivery guide for carrying the stent to a treatment site and releasing the stent at that point. To facilitate the lock-down function, the delivery guide is configured such that it is actuated by a member interior to an outer sleeve onto which the hemostatic valve of a catheter (e.g., a microcatheter or balloon catheter) can be collapsed. The inner member may be a core member (i.e., filling the center of or being coaxial with the sleeve) or one of a number of inner members.

By actuating the interior member (e.g., by withdrawing the same or by a physical shortening, such as by a heat-activated shape memory plastic or alloy wire), a restraint holding a stent over a separate, distal extension wire is moved off of the stent it holds in a collapsed configuration. Accordingly, simple withdrawal of the inner member will deploy the stent. Yet, a more user-friendly handle could be provided. In any case, the inventive system preferably offers a simple and space efficient proximal shaft that consists of an outer tubular sleeve member and a corewire therein. Such a system is easily fit to a manipulator and/or directly manipulated by a surgeon.

In the present invention, an implant delivery system is provided in which a stent or other radially expandable implant is held in a collapsed position over a wire extending from a sleeve receiving the core member, where the extension wire preferably includes an atraumatic tip. As opposed to a system in which a simple full-length sheath is employed, the restraint only covers the implant or the implant and some distal portion of the delivery device proximal to the stent. The length of the restraint may be selected according to the teachings of U.S. patent application Ser. No. 10/792,684, entitled "Sliding Restraint Stent Delivery Systems" filed on even date herewith and incorporated by reference in its entirety.

The stent or other such implant as may be employed is preferably self-expanding upon release of the restraint. Thus, full or complete placement of the stent can be achieved upon its release from the delivery device.

Minimization of delivery device crossing profile and providing internal actuation of a device with a fixed distal tip is accomplished by a cooperative relationship between the inner and outer members of the device in which one or more bridge segments associated with the restraint provides a "cross-over" from a system outer diameter (that of the restraint located exterior of the stent) to a diameter within the sleeve (with attachment to the inner/core member).

The bridge section or segment is sized to allow retracting the restraint fully off of the stent without the sleeve interfering with simple axial movement of the restraint. The bridge may be sized so that a distal end of the sleeve stops restraint withdrawal upon release of the stent. Alternatively, the system may be configured to allow further withdrawal of the restraint.

The bridge segment may be provided in any of a number of manners. It may be a separate element attached to both the restraint and the inner/core member. Alternatively it may be an integral extension of the restraint, extending distally for connection to the inner member of the delivery system. Still further, the bridging element may be an extension from or an extension of the inner member of the device. Where the inner member is a "corewire", the extension will likely neck-down or be offset to accomplish the bridge's cross-over or pass-through function.

One-sided, two-sided or three-sided bridge and sleeve/extension member connection approaches are contemplated as well. A one-sided approach may provided for the smallest possible overall delivery guide dimensions. Yet, multiple bridge member (even exceeding three) approaches may offer advantages in terms of balancing actuation loads and providing consistent flexibility performance. Another approach to achieve such balancing uses a single member, where that member is a tube or other hollow structure surrounding a structurally significant portion of the extension member.

As for the connection between the stent-carrying extension and proximal sleeve, a non-exhaustive set of options are detailed in the figures below. Alternative approaches may be employed in producing systems according to the present invention. In the broadest sense of the invention, the "connection" between the stent-carrying extension portion of the device and the proximal sleeve is intended to be generic. For instance, it may be in the form of a transition between differently shaped portions of a unitary piece of material. That is to say, the extension member/wire and sleeve members may be integral. Still, they will have a "connection" as intended herein between them.

The connection between the extension member carrying the stent and the sleeve may be made at the distal end of the sleeve. Alternatively, the connection may be set at a distal portion of the sleeve that is proximal to its end. In which case, the bridge sections and restraint length are set so as to cover, conceal or overlay the bridge sections within the sleeve.

Of course, the sleeve portion distal of the connection may be in the form of another tubular member attached at a proximal sleeve section. This approach may be desired for reason of using a thinner walled polymer distal sleeve section overlaying the bridge section(s) and even part of the restraint, while employing a metal hypotube for the proximal sleeve section where torquability and pushability requirements predominate.

A sleeve covering the bridge portion(s) can be used to help maintain alignment of components during navigation of anatomy. Indeed, if sufficiently robust, a distal sleeve section covering or a protective coil surrounding or overriding at least a portion of the extension member and bridge segment(s) can avoid a "cord effect" of the bridge(s) separating from alignment with the extension member upon system actuation to release a stent.

Other means of maintaining alignment of features are provided in other variations of the invention. In the variation of the invention noted above, the bridge segment is provided by a tubular member. By virtue of its geometry alone, it remains centered about the extension wire upon which it rides.

In another variation of the invention especially adapted to maintain element alignment, the bridge segment is optionally an extension of the core wire crossing from the inside of the sleeve to outside of it to the restraint. The bridge member may be tapered, smaller in diameter than the core wire or substantially the same in diameter. As in the variation of the invention above, in this variation, the hollow geometry of one of the system components ensures the members stay together during navigation and actuation irrespective of conditions.

Where the extension from the sleeve includes a tubular member, it also includes a wire extending from the distal end of the tubular extension member. The stent is then carried upon the reduced diameter wire extension. With the stent carried upon such a relatively small diameter body, the maximum system diameter can be minimized.

The present invention also includes a variation in which the bridge segment is nothing more than a direct connection (such as at least one pin, bent-over section of the core wire, a glue or solder joint, etc.) between the core member and the restraint. In this variation of the invention, for example, it may be the case that no tubular extension member is provided, but that instead the distal end of the sleeve is slotted. The extension member will then simply take the form of a wire connected distal to the slotted region through which the bride section slides to withdraw the restraint. Other variations are possible combining various aspects of the structures described above.

In any case, a stent stop or blocker surface is generally provided to abut the stent to hold it stationary within or relative to the delivery device upon withdrawal of the restraint. This surface may be provided in connection with the sleeve and/or the extension section. The stent stop or blocker may simply be provided by a distal portion of the proximal outer member/sleeve. Alternatively, the blocker may be in the form of a ground-in shoulder section or a ring or band, etc. connected to the extension member. Again, other possibilities exist as well, including forming the member of a radiopaque material or providing multiple interface or blocker surface features formed in the extension member under the stent. Such approaches in providing stent stop or blocker surface(s) are known in the art as described in U.S. Pat. Nos. 4,768,507; 5,484,444 and 6,302,893 as are releasable stent-holding adhesive surfaces as described in U.S. Pat. No. 5,026,377, and polymers in which to embed or grip a stent as described in U.S. Pat. Nos. 6,042,589 and 6,607,551—each patent incorporated by reference herein for its disclosure of such stent-stabilizing features.

The form of the restraint is also highly variable. In a most basic variation, it is a simple tubular member. When this form of restraint is slid axially off of the stent, the device will experience no change in its distal diameter. However, in another variation of the invention, the restraint may be adapted to collapse radially. A full discussion of such diameter adaptive restraint technology (DART™) systems is provided in U.S. patent application Ser. No. 10/792,657, entitled "Stent Delivery System with Diameter Adaptive Restraint," filed on Mar. 2, 2004 and incorporated by reference herein in its entirety. Still further, the restraint may comprise one or more members wrapped or otherwise disposed about the stent. In such a multi-member restraint approach, the portions may be interconnected, interwoven or separate from one another.

Delivery systems and guides according to the present invention are amenable to scaling to sizes not previously achieved. Consequently, the systems may be used in lieu of a guidewire, such as in a "guidewireless" delivery approach. Still further, rather than providing an "over-the-wire" delivery system as referenced above, the present systems may be regarded as "on-the-wire" delivery systems, since—in effect—delivery is accomplished by a system in which the stent is carried by a delivery guide occupying a catheter lumen that would commonly otherwise be used to accommodate a guidewire.

Whether used in such a manner or otherwise (such as by configuring the subject systems for treating larger peripheral vessels), the present invention includes systems comprising any combination of the features described herein. Methodology described in association with the devices disclosed also forms part of the invention. Such methodology may include that associated with completing an angioplasty, bridging an aneurysm, deploying radially-expandable anchors for pacing leads or an embolic filter, or placement of a prosthesis within neurovasculature, an organ selected from the kidney and liver, within reproductive anatomy such as selected vasdeferens and fallopian tubes or other applications.

DEFINITIONS

The term "stent" as used herein refers to any coronary artery stent, other vascular prosthesis, or other radially expanding or expandable prosthesis or scaffold-type implant suitable for the noted treatments or otherwise. Exemplary structures include wire mesh or lattice patterns and coils, though others may be employed in the present invention.

A "self expanding" stent is a scaffold-type structure (serving any of a number of purposes) that expands by its own action from a reduced-diameter configuration to an increased-diameter configuration. The "diameter" need not be circular—it may be of any open configuration. Self-expanding materials may be so by virtue of simple elastic behavior, superelastic behavior, a shape memory effect (i.e., heat-activated transformation from martinsite to austenite) or some other manner. Since the stents will remain in the subject's body, the material should be biocompatible or at least be amenable to biocompatible coating. As such, suitable self expanding stent materials for use in the subject invention include Nickel-Titanium (i.e., NiTi) alloy (e.g., NITINOL) and various other alloys or polymers.

A "wire" as used herein generally comprises a common metallic member. However, the wire may be coated or covered by a polymeric material (e.g., with a lubricious material such as TEFLON®, i.e. PolyTetraFlouroEthelyne—PTFE) or otherwise. Still further, the "wire" may be a hybrid structure with metal and a polymeric material (e.g. Vectran™, Spectra™, Nylon, etc.) or composite material (e.g., carbon fiber in a polymer matrix). The wire may be a filament, bundle of filaments, cable, ribbon or in some other form. It is generally not hollow.

A "core" wire as referred to herein is a member internal to an outer member, such as a tubular member. As a core wire, the member, fills or at least substantially fills all of the interior space of the tubular member.

A "hypotube" or "hypotubing" as referred to herein means small diameter tubing in the size range discussed below, generally with a thin wall. The hypotube may specifically be hypodermic needle tubing. Alternatively, it may be wound or braided cable tubing, such as provided by Asahi Intec Co., Ltd or otherwise. As with the "wire" discussed above, the material defining the hypotube may be metallic, polymeric or a hybrid of metallic and polymeric or composite material.

A "sleeve" as referred to herein may be made of such hypotubing or otherwise. The sleeve may be a tubular member, or it may have longitudinal opening(s). It is an outer member, able to slidingly receive and hold at least a portion of an inner member.

An "atraumatic tip" may comprise a plurality of spring coils attached to a tapered wire section. At a distal end the coils typically terminate with a bulb or ball that is often made of solder. In such a construction, the coils and/or solder are often platinum alloy or another radiopaque material. The coils may also be platinum, or be of another material. In the present invention, the wire section to which the coils are attached may be tapered, but need not be tapered. In addition, alternate structures are possible. For instance, molding or dip-coating with a polymer may be employed. In one example, the atraumatic tip may comprise a molded tantalum-loaded 35 durometer Pebax™ tip. However constructed, the atraumatic tip may be straight or curved, the latter configuration possibly assisting in directing or steering the delivery guide to a desired intravascular location.

To "connect" or to have or make a "connection" between parts refers to fusing, bonding, welding (by resistance, laser, chemically, ultrasonically, etc), gluing, pinning, crimping, clamping or otherwise mechanically or physically joining, attaching or holding components together (permanently or temporarily).

BRIEF DESCRIPTION OF THE DRAWINGS

Each of the figures diagrammatically illustrates aspects of the invention. Of these:

FIGS. 11A and 11B are cross-sectional side views of successive distal portions of another variation of the present invention;

FIG. 13 is a cross-sectional side view of another variation of the present invention;

FIGS. 14A-14C are cross-sectional views of the variation of the invention shown in FIG. 13, taken along lines B-B, C-C and D-D, respectively;

Variation of the invention from the embodiments pictured is, of course, contemplated.

DETAILED DESCRIPTION OF THE INVENTION

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Figure 1:
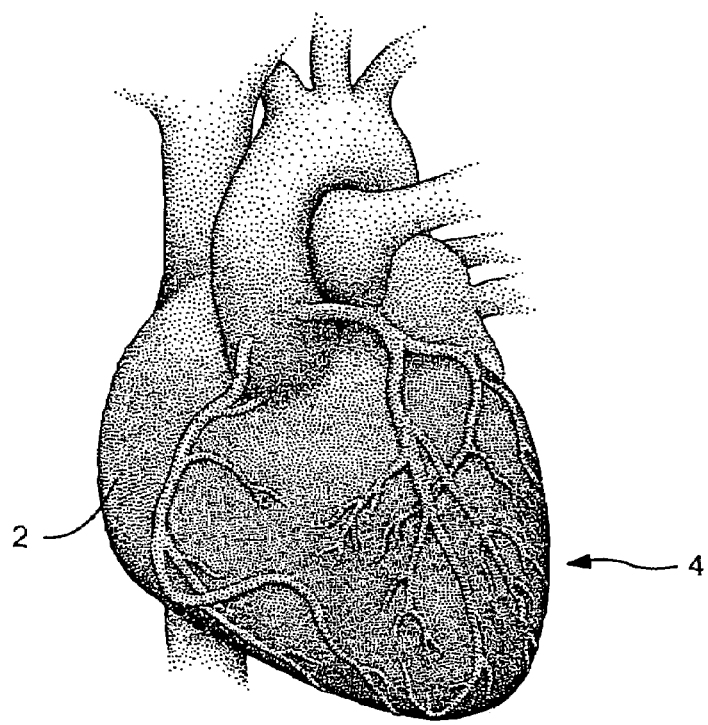
FIG. 1 shows a heart in which its vessels may be the subject of one or more angioplasty and stenting procedures.

Turning now to FIG. 1, it shows a heart 2 in which its vessels may be the subject of one or more angioplasty and/or stenting procedures. To date, however, significant difficulty or impossibility is confronted in reaching smaller coronary arteries 4. If a stent and a delivery system could be provided for accessing such small vessels and other difficult anatomy, an additional 20 to 25% coronary percutaneous procedures could be performed with such a system. Such a potential offers opportunity for huge gains in human healthcare and a concomitant market opportunity in the realm of roughly $1 billion U.S. dollars—with the further benefit of avoiding loss of income and productivity of those treated.

Features of the present invention are uniquely suited for a system able to reach small vessels (though use of the subject systems is not limited to such a setting.) By "small" coronary vessels, it is meant vessels having an inside diameter between about 1.5 or 2 and about 3 mm in diameter. These vessels include, but are not limited to, the Posterior Descending Artery (PDA), Obtuse Marginal (OM) and small diagonals. Conditions such as diffuse stenosis and diabetes produce conditions that represent other access and delivery challenges which can be addressed with a delivery system according to the present invention. Other extended treatment areas addressable with the subject systems include vessel bifurcations, chronic total occlusions (CTOs), and prevention procedures (such as in stenting vulnerable plaque).

Assuming a means of delivering one or more appropriately-sized stents, it may be preferred to use a drug eluting stent in such an application to aid in preventing restenosis. However, bare-metal stents may be employed in the present invention. The present invention is advantageously employed with self-expanding stents. However, the teachings herein may be adapted for application in the context of balloon-expandable stents.

In any case, features of the present invention are provided in order to hold an implant (e.g., a stent) to be delivered in an access or deployment configuration, after which, the implant assumes its deployed or expanded configuration. Hold-down features may restrain a stent under compressive forces, whereupon release, the stent "springs" open. Alternatively, the stent (or other implant) may simply be secured to the delivery member, where some other mechanism is used to open the stent (e.g., ceasing a flow of chilled saline, thereby allowing a shape memory devices (e.g., NiTi) to warm in order that a material phase change from martinsite to austenite will cause the stent to open).

While some might argue that the particular role and optimal usage of self expanding stents has yet to be defined, they offer an inherent advantage over balloon expandable stents. The latter type of devices produce "skid mark" trauma (at least when delivered uncovered upon a balloon) and are associated with a higher risk of end dissection or barotraumas caused at least in part by high balloon pressures and related forces when deforming a balloon-expandable stent for deployment.

Yet, with an appropriate deployment system, self-expanding stents may offer one or more of the following advantages over balloon-expandable models: 1) greater accessibility to distal, tortuous and small vessel anatomy—by virtue of decreasing crossing diameter and increasing compliance relative to a system requiring a deployment balloon, 2) sequentially controlled or "gentle" device deployment, 3) use with low balloon pre-dilatation (if desirable) to reduce barotraumas, 4) strut thickness reduction in some cases reducing the amount of "foreign body" material in a vessel or other body conduit, 5) opportunity to treat neurovasculature—due to smaller crossing diameters and/or gentle delivery options, 6) the ability to easily scale-up a successful treatment system to treat larger vessels or vice versa, 7) a decrease in system complexity, offering potential advantages both in terms of reliability and system cost, 8) reducing the effects of intimal hyperplasia, and 9) conforming to tapering anatomy—without imparting complimentary geometry to the stent (though this option exists as well).

Figure 2:
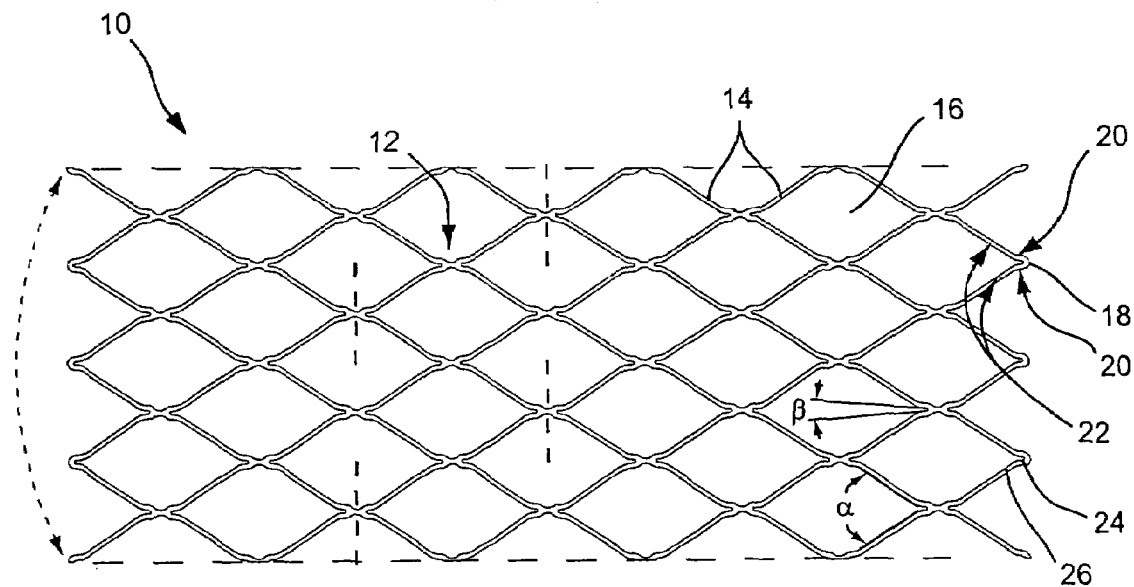
FIG. 2 shows an expanded stent cut pattern as may be used in producing a stent for use in the present invention.

At least some of these noted advantages may be realized using a stent 10 as shown in FIG. 2 in connection with the subject deployment system described in further detail below. Naturally, other stent configurations might be used instead. However, the one pictured is well suited for use in small vessels. It may be collapsed to an outer diameter of about 0.018 inch (0.46 mm), or even smaller to about 0.014 inch (0.36 mm)—including the restraint/joint used—and expand to a size (fully unrestrained) between about 1.5 mm (0.059 inch) or 2 mm (0.079 inch) or 3 mm (0.12 inch) and about 3.5 mm (0.14 inch).

In use, the stent will be sized so that it is not fully expanded when fully deployed against the wall of a vessel in order that it will provide a measure of radial force thereto. The force will secure the stent and offer potential benefits in reducing intimal hyperplasia and vessel collapse or even pinning dissected tissue in apposition.

The stent employed in connection with the subject delivery system preferably comprises NiTi that is superelastic at room temperature and above. Also, it is preferably electropolished. The stent may be a drug eluting stent (DES). Such drug can be directly applied to the stent surface(s), or introduced into an appropriate matrix.

In a 0.014 inch delivery system (one in which the maximum nominal outer diameter of the stent/coating and guide member/restraint have a diameter that does not exceed 0.014 inch), the thickness of the NiTi is about 0.0025 inch (0.64 mm) for a stent adapted to expand to 3.5 mm. Such a stent is designed for use in a roughly 3 mm vessel or other body conduit, thereby providing the desired radial force in the manner noted above. Further information regarding radial force parameters in coronary stents may be noted in the article, "Radial Force of Coronary Stents: A Comparative Analysis," Catheterization and Cardiovascular Interventions 46: 380-391 (1999), incorporated by reference herein in its entirety.

As for the stent that may be employed, an optional expanded stent cut pattern 10 is shown in FIG. 2. In one manner of production, the stent is laser (or Electrical Discharge Machining, i.e., EDM) cut from round NiTi tubing, with the flattened-out pattern shown wrapping around the tube as indicated by dashed lines. In such a procedure, the stent is preferably cut in its fully-expanded shape. By initially producing the stent to full size, the approach allows cutting finer details in comparison to simply cutting a smaller tube with slits and then heat-expanding/annealing it into its final (working) diameter. Avoiding post-cutting heat forming also reduces production cost.

Regarding the finer details of the subject stent, necked down bridge or junction sections 12 are provided between adjacent struts 14, wherein the struts define a lattice of closed cells 16. The ends 18 of the cells are preferably rounded-off so as to be atraumatic. To increase stent conformability to tortuous anatomy, the bridge sections can be strategically separated or opened as indicated by broken line. To facilitate such tuning of the stent, the bridge sections are sufficiently long so that fully rounded ends 18 may be formed internally to the lattice just as shown on the outside of the stent if the connection(s) is/are severed to separate adjacent cells 16.

The advantage of the double-concave profile of each strut bridge or junction section 12 is that it reduces material width (relative to what would otherwise be presented by a parallel side profile) to improve trackability and conformability of the stent within the subject anatomy while still maintaining the option for separating/breaking the cells apart.

Further optional features of stent 10 are employed in the cell end regions 18 of the design. Specifically, strut ends 20 increase in width relative to medial strut portions 22. Such a configuration results in a majority of bending (during collapse of the stent) occurring along the length of the struts rather than at the corners of the cells. Longer struts to allow for lower stresses within the stent (and, hence, possibility for higher compression ratios). Shorter struts allow for greater radial force (and concomitant resistance to a radially applied load) upon deployment.

In order to provide a stent that collapses as much as possible (to solid or near-solid structure, such as shown in the fully-loaded systems of the figures) accommodation is made for the stiffer strut ends 20 provided in the design shown in FIG. 2. Namely, the gap 24 between the strut ends 22 is set at a smaller angle as if the stent were already partially collapsed in that area. Thus, the smaller amount of angular deflection that occurs at ends 20 will bring the sections parallel (or nearly so) when the strut medial portions 22 are so-arranged. Radiused sections 26 provide a transition from a medial strut angle $\alpha$ (ranging from about 85 degrees to about 60 degrees) to an end strut angle $\beta$ (ranging from about 30 to about 0 degrees) at the strut junctions and/or extensions therefrom.

In addition, it is noted that gap 24 and angle $\beta$ may actually be configured to completely close prior to fully collapsing angle $\alpha$. The stent shown is not so-configured. Still, the value of doing so would be to limit the strains (and hence, stresses) at the strut ends 22 and cell end regions 18 by providing a physical stop to prevent further strain. Alternative, advantageous stent designs that may be used in connection with the present invention are presented in U.S. Provisional Patent Application Ser. No. 60/619,437, entitled, "Small Vessel Stent Designs", filed Oct. 14, 2004 and incorporated herein by reference in its entirety.

By utilizing any of these designs, very high compression ratios of the stent may be achieved. Compression ratios (from a fully expanded outside diameter to compressed outside diameter—expressed in those terms used by physicians) of as much as 3.5 mm: 0.014 inch (about 10×) are possible—with or without a drug coating and/or restraint used. Compression ratios of 3.0 mm:0.014 inch (about 8.5×), 3.5 mm:0.018 inch (about 7.5×), 3.0 mm:0.018 inch (about 6.5×), 2.5 mm:0.014 inch (about 7×), 2.5 mm:0.018 inch (about 5.5×), 2.0 mm:0.014 inch (about 5.5×), 2.0 mm:0.018 inch (about 4.5×) offer utility not heretofore possible with existing systems as well.

These selected sizings (and expansion ratios) correspond to treating 1.5 to 3.0 mm vessels by way of delivery systems adapted to pass through existing balloon catheter and microcatheter guidewire lumen. In other words, the 0.014 inch and 0.018 inch systems are designed to corresponding common guidewire sizes. The system may also be scaled to other common guidewire sizes (e.g., 0.22 inch/0.56 mm or 0.025 inch/0.64 mm) while offering advantages over known systems.

While designing the delivery systems to have a crossing profile corresponding to common guidewire sizes, especially for full-custom systems, intermediate sizes may be employed. Still further, it is contemplated that the system sizing may be set to correspond to French (FR) sizing. In that case, system sizes contemplated range at least from 1 to 1.5 FR, whereas the smallest know balloon-expandable stent delivery systems are in the size range of about 3 to about 4 FR.

At least when produced at the smallest sizes (whether in a even/standard guidewire or FR size, or otherwise), the system enables a substantially new mode of stent deployment in which delivery is achieved through an angioplasty balloon catheter or small microcatheter lumen. Further discussion and details of "through the lumen" delivery is presented in the above-referenced "Balloon Catheter Lumen Based Stent Delivery Systems" patent application.

In "small vessel" cases or applications (where the vessel to be treated has a diameter up to about 3.0 mm), it may also be advantageous to employ a stent delivery system sized at between about 0.022 to about 0.025 inch in diameter. Such a system can be used with catheters compatible with 0.022 inch diameter guidewires.

While such a system may not be suitable for reaching the very smallest vessels, in reaching the larger of the small vessels (i.e., those having a diameter of about 2.5 mm or larger), even this variation of the invention is quite advantageous in comparison to known systems. By way of comparison, the smallest known over-the-guidewire delivery systems are the Micro-Driver™ and Pixel™ systems by Guidant. These are adapted to treat vessels between 2 and 2.75 mm, the latter system having a crossing profile of 0.036 inches (0.91 mm). A system described in U.S. Patent Publication No. 2002/0147491 for treating small vessels is purported to be capable of being made as small as 0.026 inch (0.66 mm) in diameter.

With respect to such systems, however, it must be appreciated that a further decrease in stent size may be practically impossible in view of materials limitations and functional parameters of the stent. Instead, the present invention offers a different paradigm for delivery devices and stents that are scalable to the sizes noted herein.

By virtue of the approaches taught herein, it is feasible to design system diameters to match (or at least nearly match) common guidewire size diameters (i.e., 0.014, 0.018 and 0.022 inch) for small vessel delivery applications. As noted above, doing so facilitates use with compatible catheters and opens the possibility for methodology employing the same as elaborated upon below and in the above-referenced "Balloon Catheter Lumen Based Stent Delivery Systems" patent application.

Of further note, it may be desired to design a variation of the subject system for use in deploying stents in larger, peripheral vessels, biliary ducts or other hollow body organs. Such applications involve a stent being emplaced in a region having a diameter from about 3.5 to about 13 mm (0.5 inch). In this regard, the scalability of the present system, again, allows for creating a system adapted for such use that is designed around a common wire size. Namely, a 0.035 to 0.039 inch (3 FR) diameter crossing profile system is advantageously provided in which the stent expands (unconstrained) to a size between about roughly 0.5 mm and about 1.0 mm greater than the vessel or hollow body organ to be treated. Sufficient stent expansion is easily achieved with the exemplary stent pattern shown in FIG. 2.

Again, as a matter of comparison, the smallest delivery systems known to applicants for stent delivery in treating such larger-diameter vessels or biliary ducts is a 6 FR system (nominal 0.084 inch outer diameter), which is suited for use in an 8 FR guiding catheter. Thus, even in the larger sizes, the present invention affords opportunities not heretofore possible in achieving delivery systems in the size range of a commonly used guidewire, with the concomitant advantages discussed herein.

Several known stent delivery systems are compatible with (i.e., may be delivered over) common-sized guides wires ranging from 0.014 inch to 0.035 inch (0.89 mm). Yet, none of the delivery systems are themselves known to be so-sized.

As for the manner of using the inventive system as optionally configured, FIGS. 3A-3L illustrate an exemplary angioplasty procedure. Still, the delivery systems and stents or implants described herein may be used otherwise—especially as specifically referenced herein.

Figure 3A:
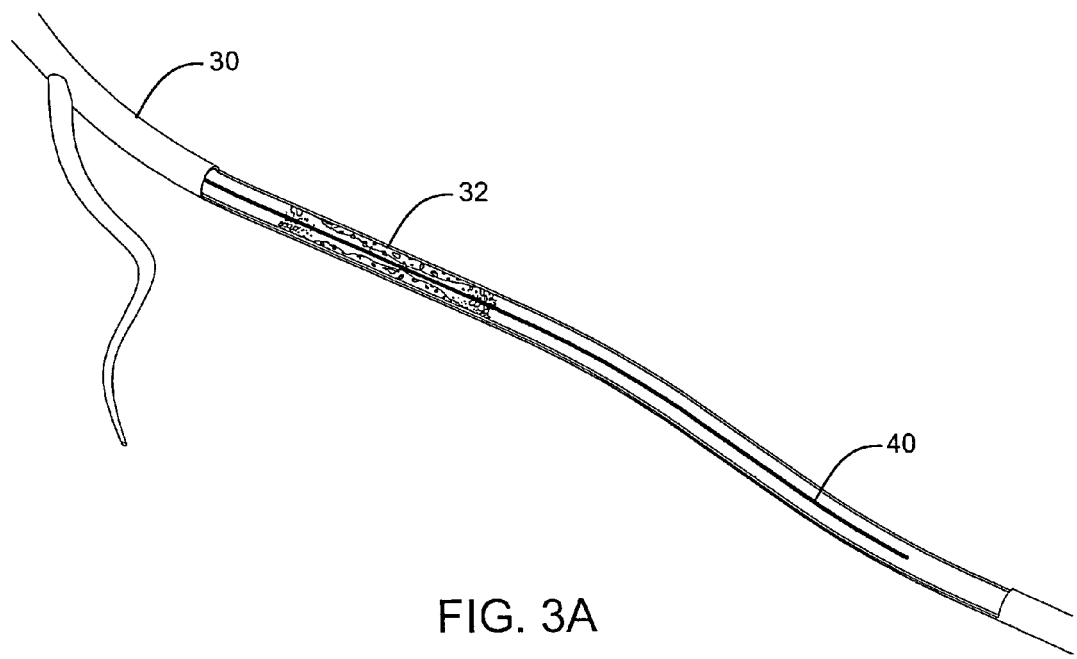
FIGS. 3A-3L illustrate stent deployment methodology to be carried out with the subject delivery guide member.
Figure 3B:
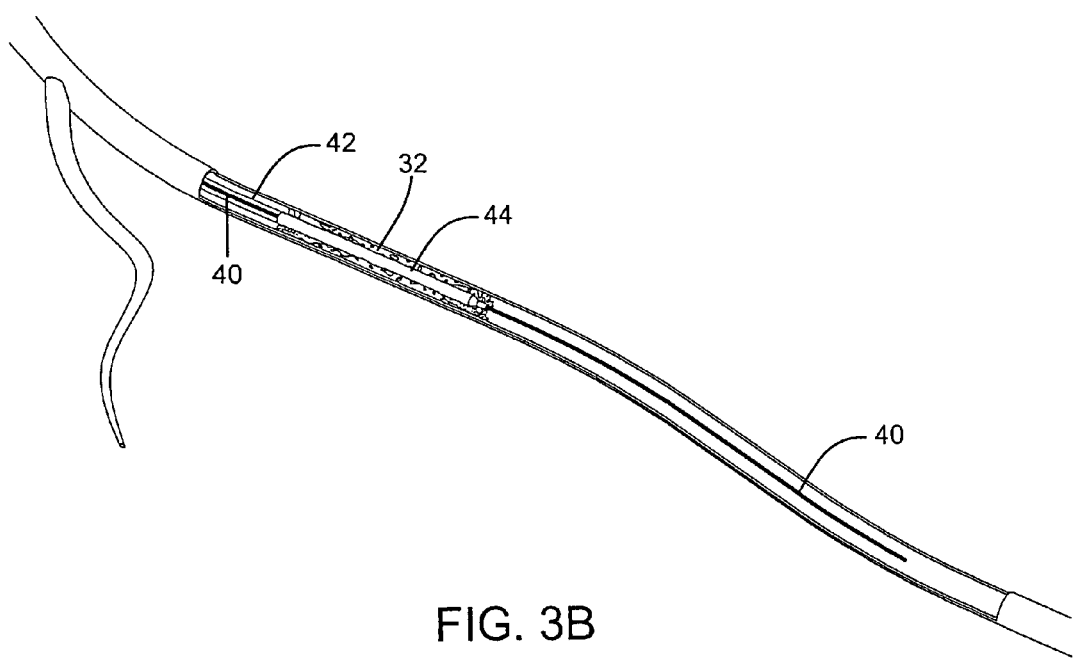

Turning to FIG. 3A, it shows a coronary artery 30 that is partially or totally occluded by plaque at a treatment site/lesion 32. Into this vessel, a guidewire 40 is passed distal to the treatment site. In FIG. 3B, a balloon catheter 42 with a balloon tip 44 is passed over the guidewire, aligning the balloon portion with the lesion (the balloon catheter shaft proximal to the balloon is shown in cross section with guidewire 40 therein).

Figure 3C:
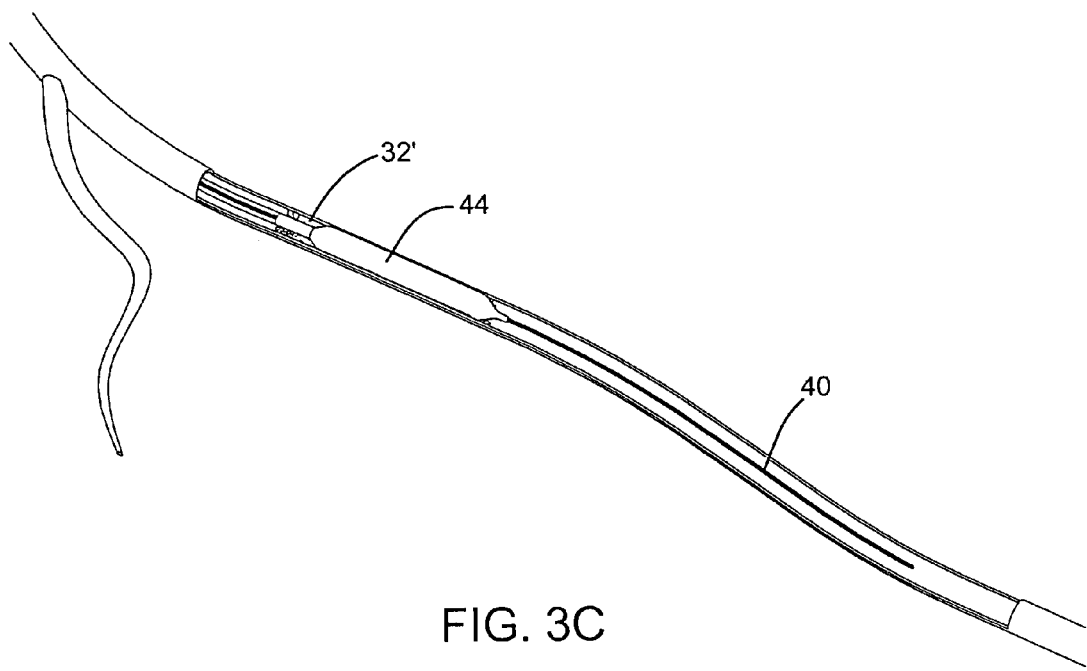

As illustrated in FIG. 3C, balloon 44 is expanded (dilatated or dilated) in performing an angioplasty procedure, opening the vessel in the region of lesion 32. The balloon expansion may be regarded as "predilatation" in the sense that it will be followed by stent placement (and optionally) a "postdilataton" balloon expansion procedure.

Figure 3D:
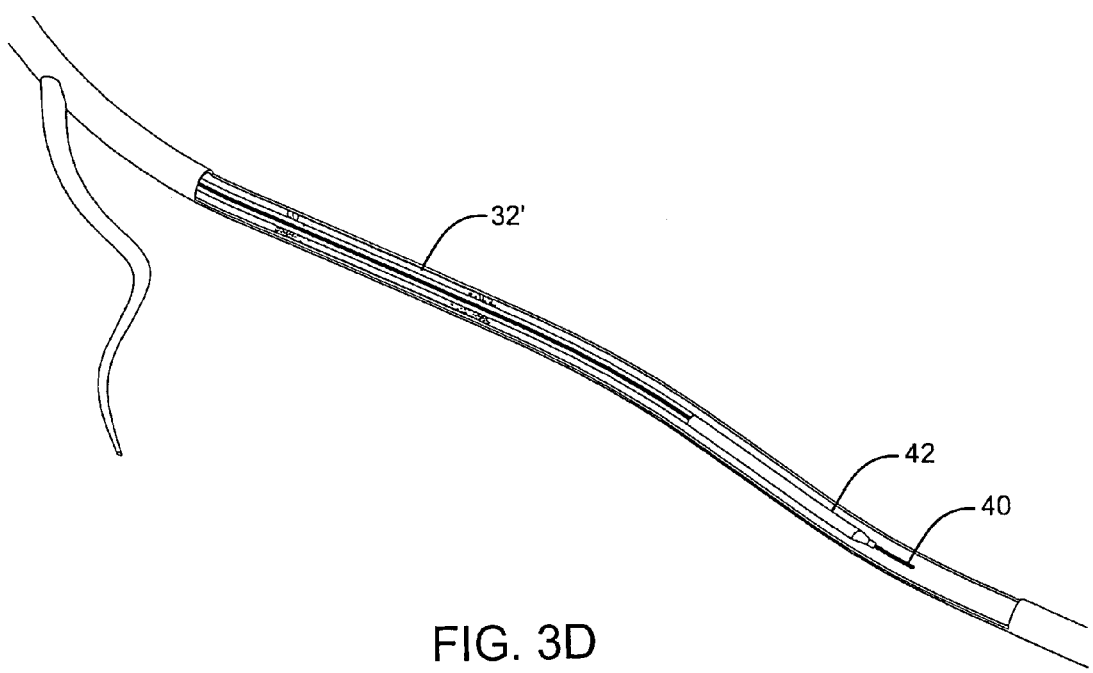
Figure 3E:
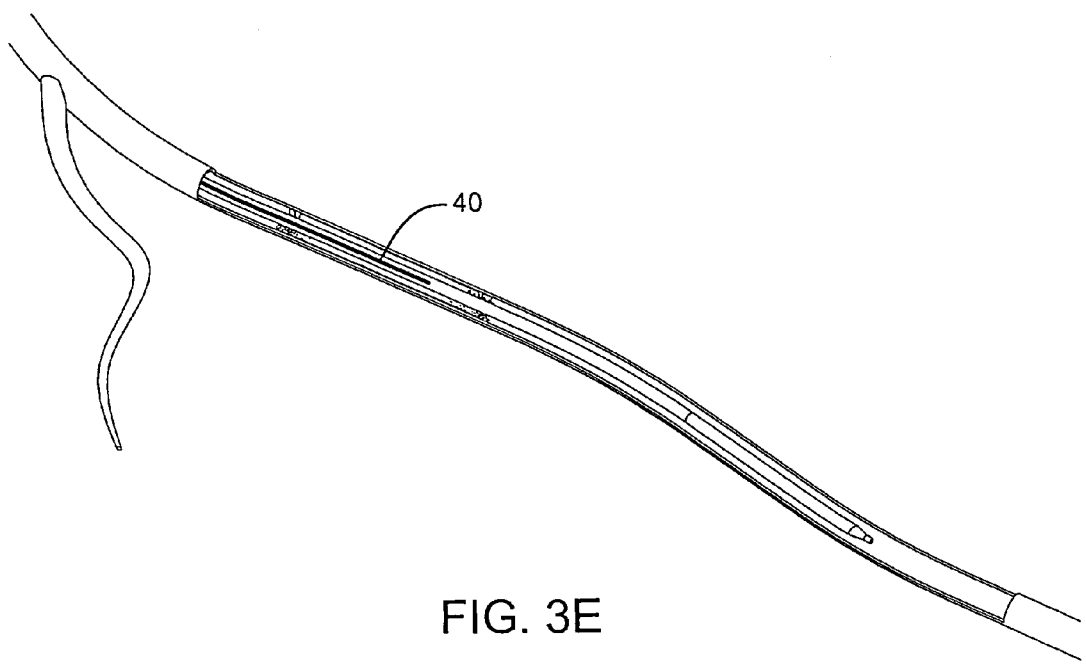
Figure 3F:
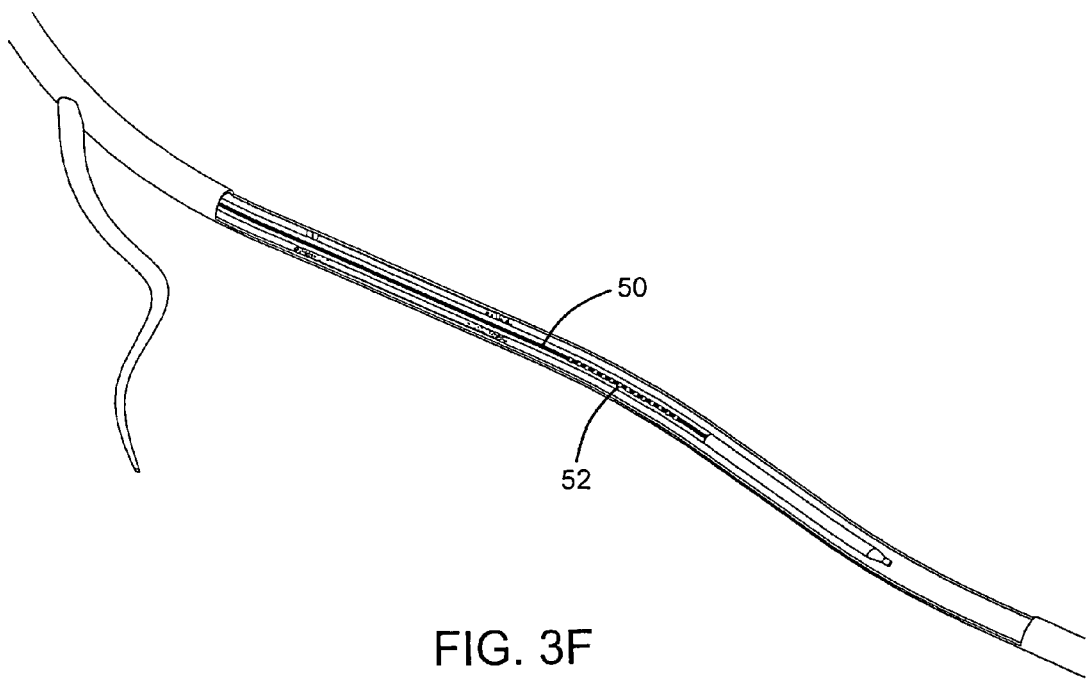

Next, the balloon is at least partially deflated and passed forward, beyond the dilate segment 32' as shown in FIG. 3D. At this point, guidewire 40 is removed as illustrated in FIG. 3E. It is exchanged for a delivery guide member 50 carrying stent 52 as further described below. This exchange is illustrated in FIGS. 3E and 3F.

However, it should be appreciated that such an exchange need not occur. Rather, the original guidewire device inside the balloon catheter (or any other catheter used) may be that of item 50, instead of the standard guidewire 40 shown in FIG. 3A. Thus, the steps depicted in FIGS. 3E and 3F (hence, the figures also) may be omitted. In addition, there may be no use in performing the step in FIG. 3D of advancing the balloon catheter past the lesion, since such placement is merely for the purpose of avoiding disturbing the site of the lesion by moving a guidewire past the same.

Figure 3G:
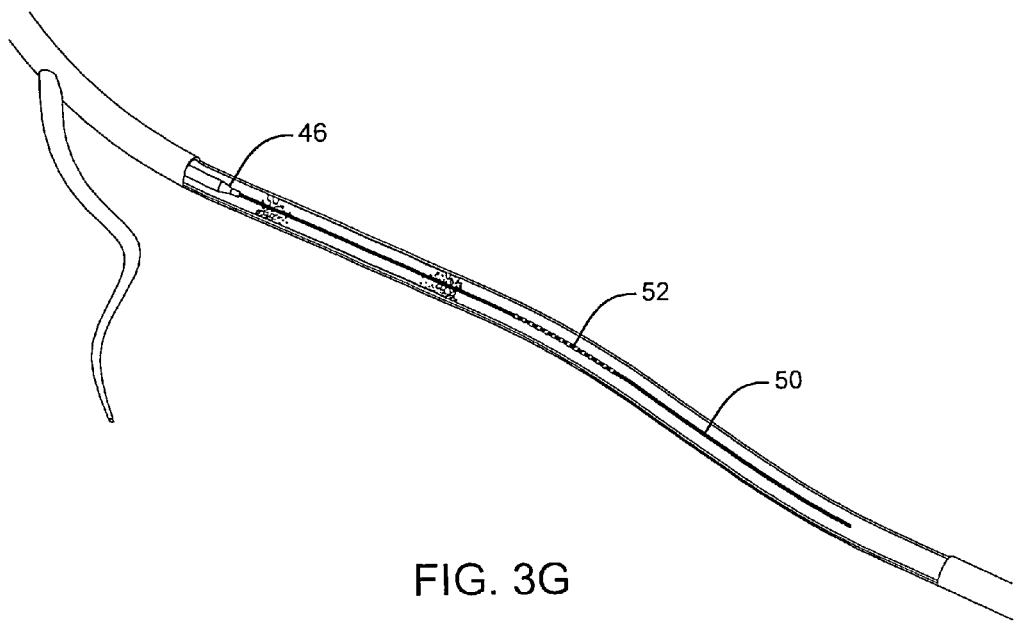
Figure 3H:
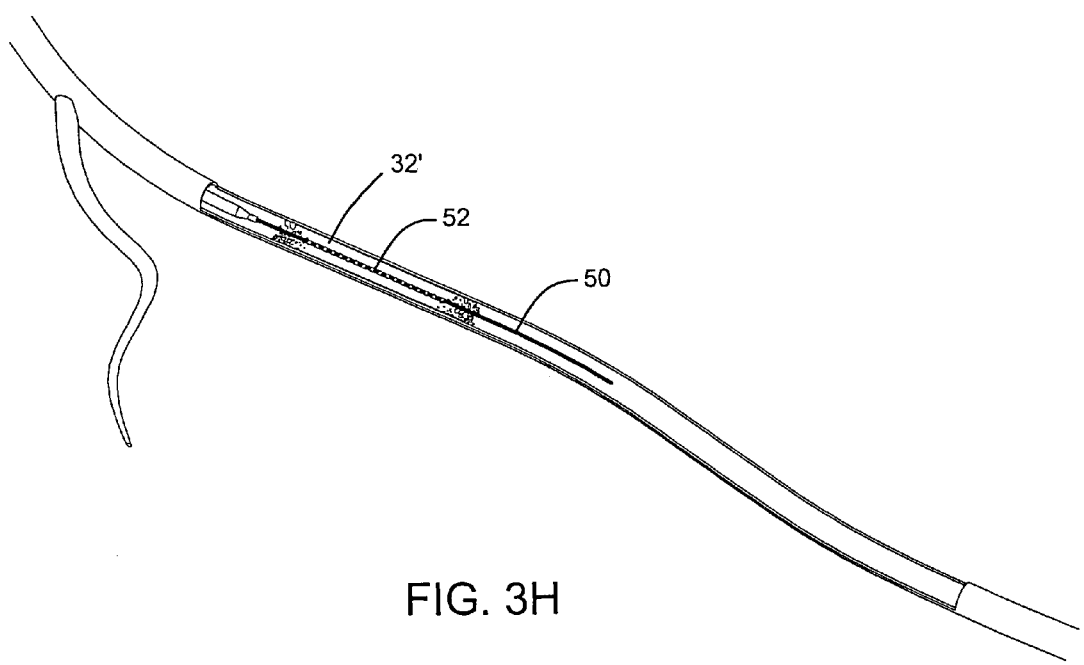

FIG. 3G illustrates the next act in either case. Particularly, the balloon catheter is withdrawn so that its distal end 46 clears the lesion. Preferably, delivery guide 50 is held stationary, in a stable position. After the balloon is pulled back, so is delivery device 50, positioning stent 52 where desired. Note, however, that simultaneous retraction may be undertaken, combining the acts depicted in FIGS. 3G and 3H. Whatever the case, it should also be appreciated that the coordinated movement will typically be achieved by virtue of skilled manipulation by a doctor viewing one or more radiopaque features associated with the stent or delivery system under medical imaging.

Figure 3I:
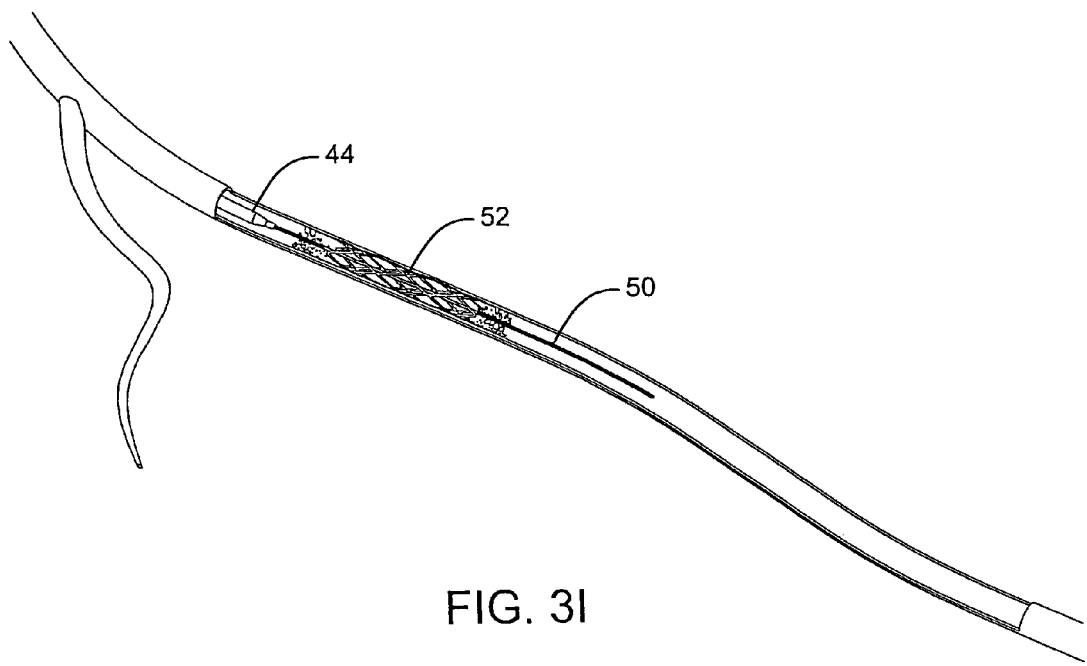
Figure 3J:
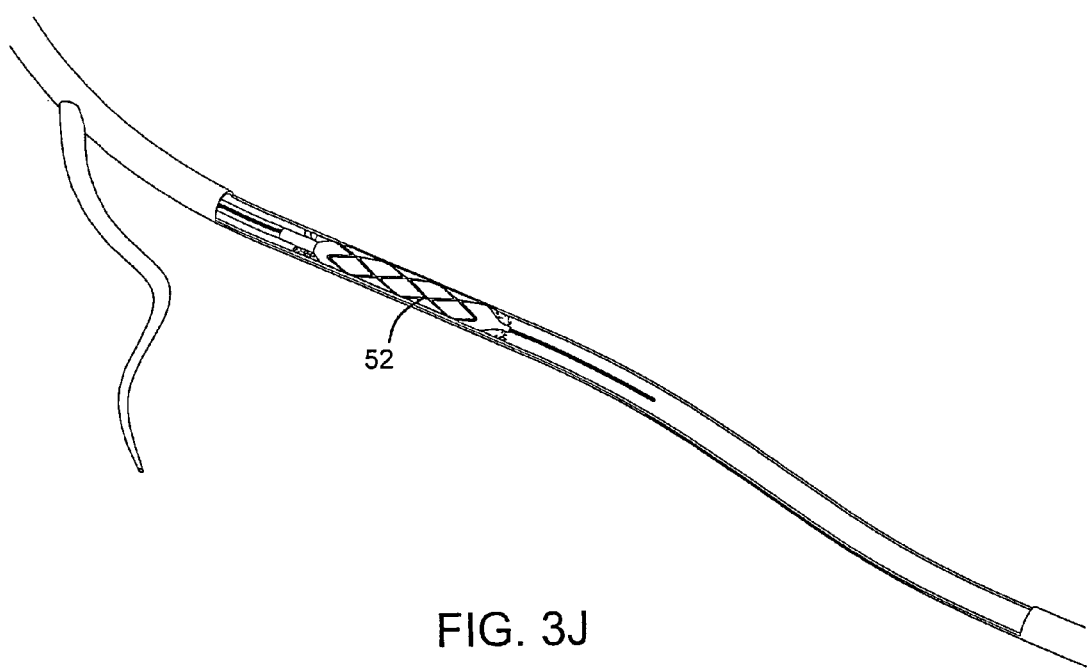
Figure 3K:
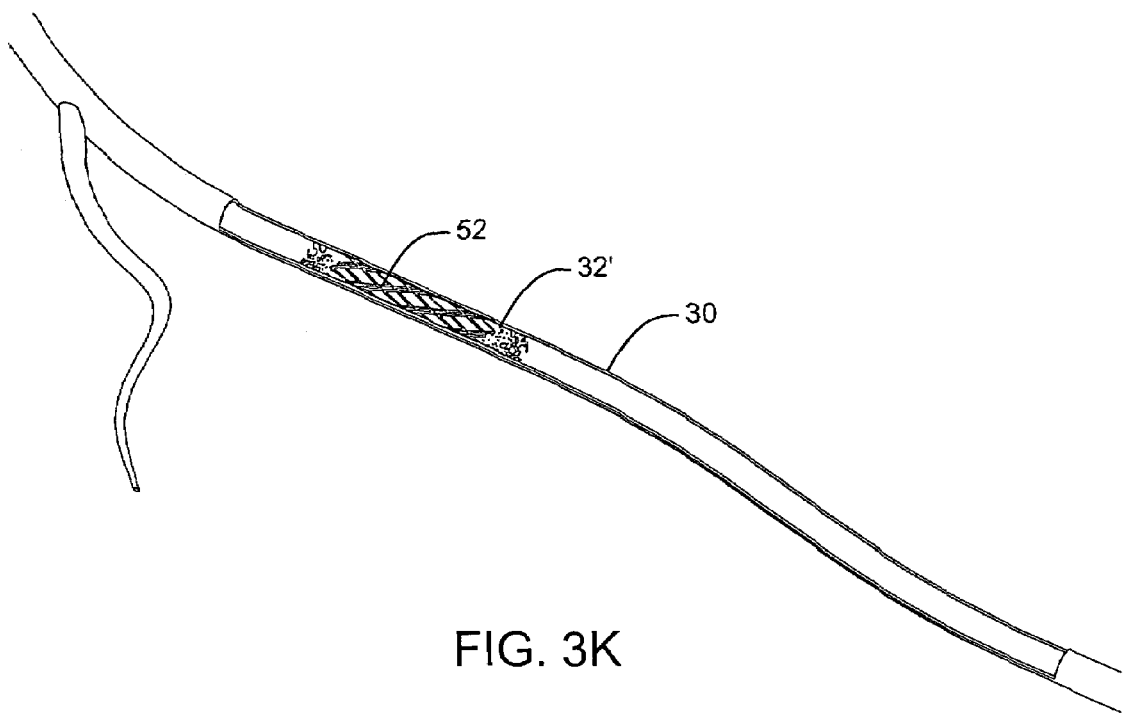

Once placement of the stent across from dilated segment 32' is accomplished, stent deployment commences. The manner of deployment is elaborated upon below. Upon deployment, stent 52 assumes an at least partially expanded shape in apposition to the compressed plaque as shown in FIG. 3I. Next, the aforementioned postdilatation may be effected as shown in FIG. 3J by positioning balloon 44 within stent 52 and expanding both. This procedure may further expand the stent, pushing it into adjacent plaque—helping to secure each.

Naturally, the balloon need not be reintroduced for postdilatation, but it may be preferred. Regardless, once the delivery device 50 and balloon catheter 42 are withdrawn as in FIG.

Figure 3L:
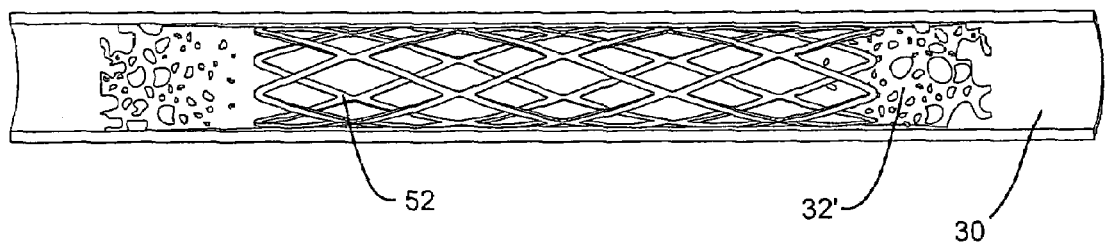

3K, the angioplasty and stenting procedure at the lesion in vessel 30 is complete. FIG. 3L shows a detailed view of the emplaced stent and the desired resultant product in the form of a supported, open vessel.

In the above description, a 300 cm extendable delivery system is envisioned. Alternatively, the system can be 190 cm to accommodate a rapid exchange of monorail type of balloon catheter as is commonly known in the art. Of course, other approaches may be employed as well.

Furthermore, other endpoints may be desired such as implanting an anchoring stent in a hollow tubular body organ, closing off an aneurysm, delivering a plurality of stents, etc. In performing any of a variety of these or other procedures, suitable modification will be made in the subject methodology. The procedure shown is depicted merely because it illustrates a preferred mode of practicing the subject invention, despite its potential for broader applicability.

Figure 4:
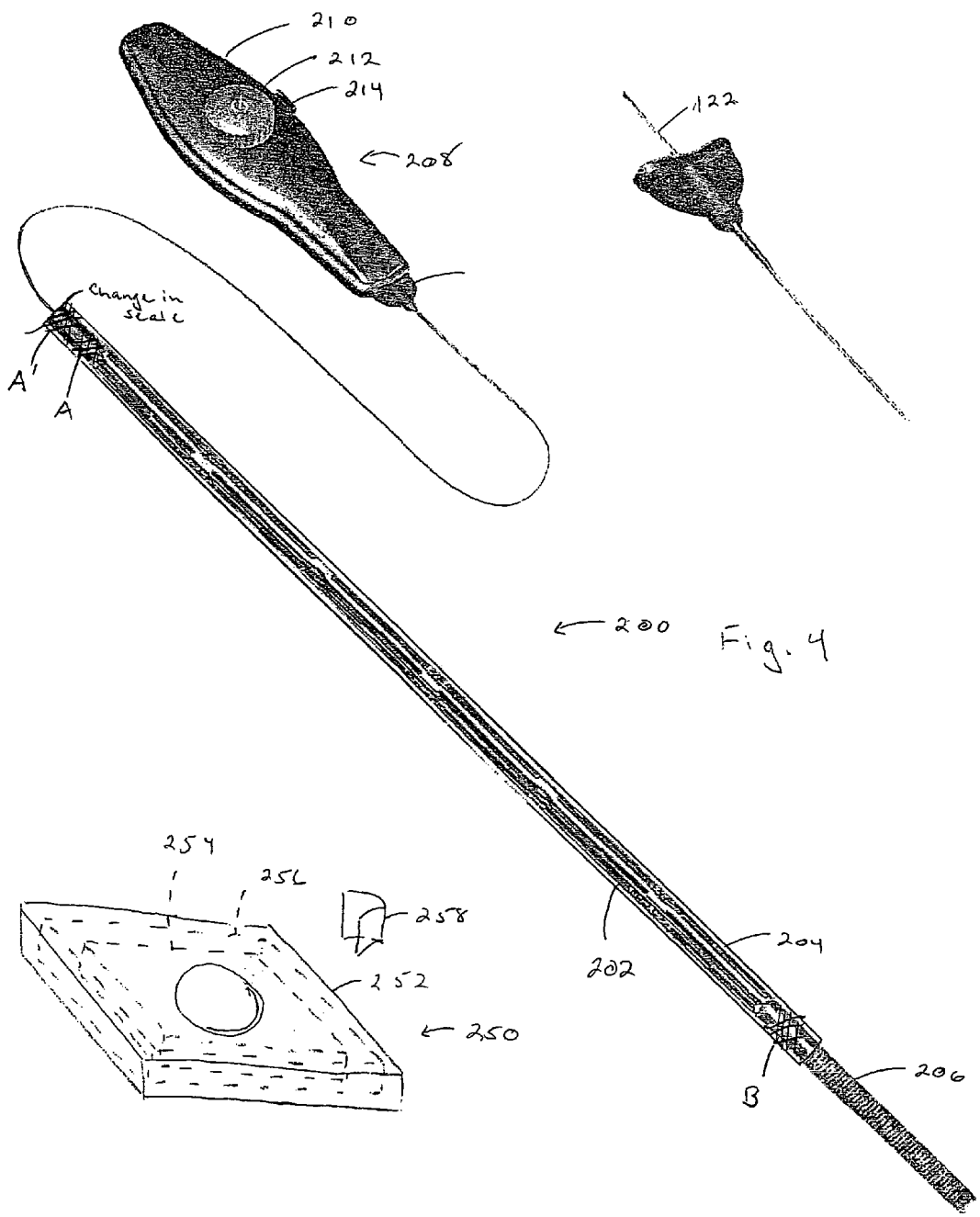
FIG. 4 provides an overview of the inventive system.

A more detailed overview of the subject delivery systems is provided in FIG. 4 Here, a delivery system 200 is shown along with a stent 202 held in a collapsed configuration upon the delivery guide member. A restraint 204 is provided over and around the stent. The restraint may fully surround the stent or only subtend a partial circumference of the stent, it may be split, splittable, comprise a plurality of member or be otherwise provided around the stent to hold or restrain it in a collapsed profile.

Regarding the overall delivery guide, however, it preferably comprises an atraumatic distal tip 206 of one variety or another. On the other end of the delivery device, a custom handle 208 is preferably provided.

The handle shown is adapted for rotable actuation by holding body 210, and turning wheel 212. It may include a lock 214. Furthermore, a removable interface member 216 facilitates taking the handle off of the delivery system proximal end 218. The interface will be lockable with respect to the body and preferably includes internal features for disengaging the handle from the delivery guide. Once accomplished, it will be possible to attach or "Doc" a secondary length of wire 220 on the delivery system proximal end, allowing the combination to serve as an "exchange length" guidewire, thereby facilitating changing-out the balloon catheter or performing another procedure. Alternatively, the wire may be an exchange-length wire.

FIG. 4 also shows packaging 250 containing at least one coiled-up delivery systems 200. When a plurality of such systems are provided (in one package or by way of a number of packages held in stock), they are typically configured in support of a methodology where an appropriate one is picked to reach a target site and deploy a stent without unintended axial movement of the same as per the methodology of the "Sliding Restraint Stent Delivery Systems" patent application referenced above. Thus, the packaging may serve the purpose of providing a kit or panel of differently configured delivery devices. In the alternative, the packaging may be configured as a tray kit for a single one of the delivery systems.

Either way, packaging may include one or more of an outer box 252 and one or more inner trays 254, 256 with peel-away coverings as is customary in packaging of disposable products provided for operating room use. Naturally, instructions for use can be provided therein. Such instructions may be printed product or be provided in connection with another readable (including computer-readable) medium. The instructions may include provision for basic operation of the subject devices and/or the selection methodology.

Regarding the specifics of the restraint employed in the delivery device, it preferably is one that does not have a section that increases in size during, or after, deployment of the stent. They are such that restraint diameter remains constant or actually decreases in diameter upon withdrawal from the stent and release of the same.

Figure 5A:
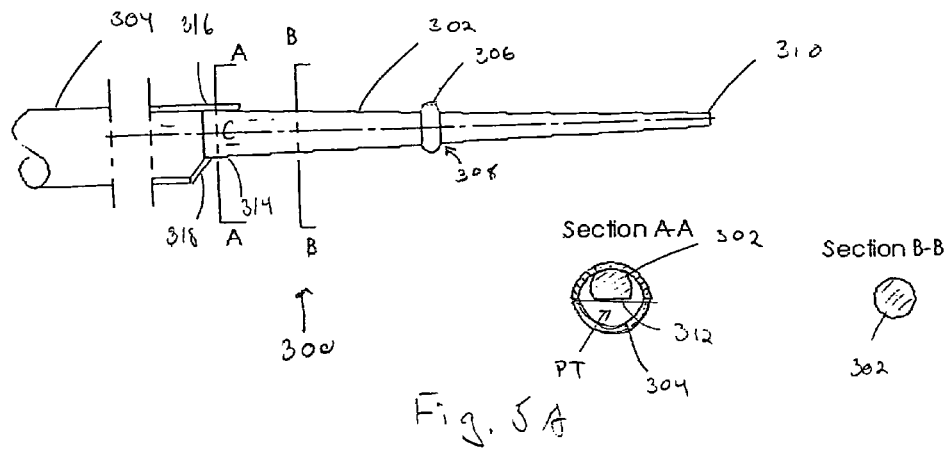
FIGS. 5A-5C provide detailed views of a first variation of the present invention.
Figure 5B:
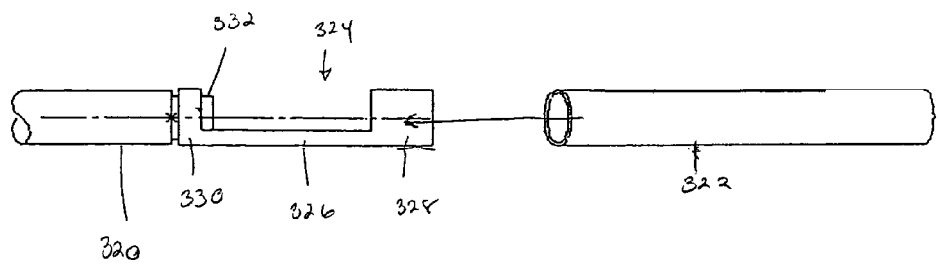
Figure 5C:
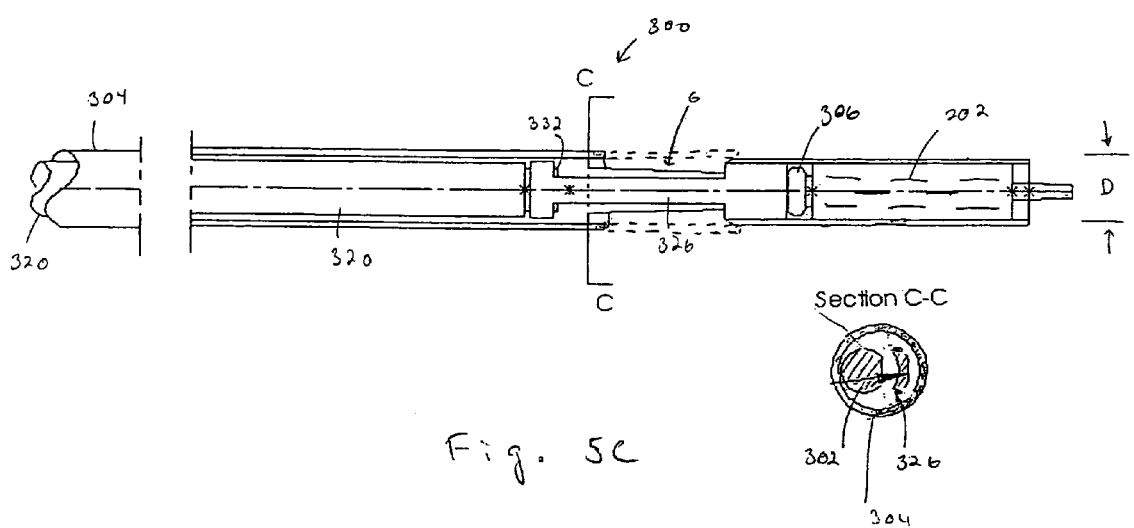

Regarding the first variation shown in FIGS. 5A-5C, FIGS. 5A and 5B show sub-assemblies, whereas the parts are combined in FIG. 5C. In FIG. 5A, a distal end 300 of the delivery device 200 is shown in partial cross-section. It includes an extension wire 302 attached/connected to a hypotube section 304. The hypotube extends proximally (to the left) and serves as the "sleeve" referred to above. For a "one-sided" system as further detailed in FIGS. 5B and 5C, the extension member 302 is offset within the tubing 304. This relation of elements is most clearly shown in Section A-A, showing a pass-through opening ("PT") between the extension 302 and sleeve 304. It is in this manner, that this variation of the invention achieves the cross-over of its active members from the outer diameter of the device to the interior of the sleeve.

Distal of the connection "C" between members 302 and 304, a shoulder section may be ground into the wire or a separate ring 306 may be attached thereto to provide a stop surface 308 for abutting the stent to be delivered. Moving toward the distal tip 310, the system may be tapered as shown. The length of the extension over which the restraint rides is variable as is the restraint. The taper may be desired for increased distal flexibility.

The overall length of the system from a distal tip (possibly incorporating an atraumatic tip, to the base of any actuation device provided may be around 135 cm (53 inch) to 200 cm (79 inch) or more preferably between 180 cm (71 inch) and 190 cm (75 inch). Overall longer or shorter system lengths are also contemplated. The length of the extension 302 and stent-overlying restraint/connector is variable. The length of the extension section may be between about 10 cm to 15 cm, about 15 cm to about 25 cm or up to 30 cm or longer as possibly influenced or dictated by system flexibility requirements.

Returning, however, to the specific device configuration shown in FIG. 5A, it may be desired to create a flat section 312 for clearance purposes where the proximal end 314 of the extension member and distal end 316 of the sleeve overlap. To increase system compliance at this intersection where connection C is made, it may be desired to relieve or create an angled section 318 at the distal end of the hypotubing. To encourage even navigation performance characteristics, the extension wire will return to round as shown in Section B-B distal of the intersection.

FIG. 5B shows the remaining elements for the distal portion 300 of this variation of the delivery device. Specifically, an inner wire 320 (pictured in this case as a corewire providing column strength to the system and aiding in its noted desired functional characteristics in terms—such as in terms of torqueability and directability to a target site), a restraint 322 and connector 324 for attachment of the pieces as shown. The connector includes a bridge section 326 that crosses from the outside diameter "D" of the device to inside, traversing pass-through PT. Bonding sections 328, 330 are provided, preferably for gluing to the restraint and a distal end 332 of the inner wire 320.

Of course, the restraint and bridge section may be provided integrally (in which case the bridge may be connected directly to the inner member—or by differently configured connector piece). Otherwise, they may be made of different materials. For example, the connector may comprise stainless steel or Nitinol (just as other members of the delivery guide) and the restraint a polymeric material. A polymeric restraint (such as polyimide or PET may be desired since it is readily obtained in very thin-wall tubing—down to 0.00025 inch).

In FIG. 5C, the various components discussed above are assembled with the distal portion shown in partial cross-section as in FIG. 5A. Section C-C shows the manner in which bridge section 326 passes by extension section 302 within the device. To provide a low-profile device, the bridge section and extension run substantially in parallel. Indeed, all of the cross-sections show the close-packed arrangement of elements. Further, a stent 202 is shown in a collapsed configuration within the restraint.

Overall, the system has a diameter ("D") dictating its crossing profile. To actuate the device, inner/core member 320 is withdrawn causing the restraint to slide off of the stent without the diameter D to increase as the clearance gap ("G") between the restraint and sleeve is closed.

Note, however, that it may be the case that no open gap G is provided. This may be accomplished by extending the sleeve over the connector as indicated by dashed lines in FIG. 5C over the gap. Indeed, this "hidden" bridge or connector variation of the invention may be desirable in order to help prevent system kinking or pushing the restraint forward after retraction (such as is in an abortive stent delivery procedure) or just generally protecting any bridge section(s).

As noted above, the sleeve may be extended by another piece of material connected thereto. Advantageously, it could be a thin-walled polymeric tube. Alternatively, the "extension" may be provided in a relative sense by moving the connection point between the sleeve and the extension wire proximally within the sleeve. In either case, the additional sleeve length and relative positioning of elements is indicated by the addition of the phantom line structure in FIG. 5C.

Figure 6A:
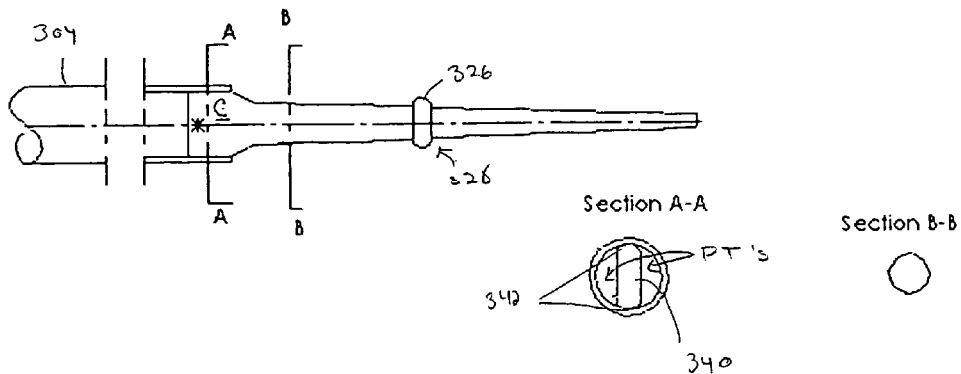
FIGS. 6A-6C provide detailed views of a second variation of present invention.
Figure 6B:
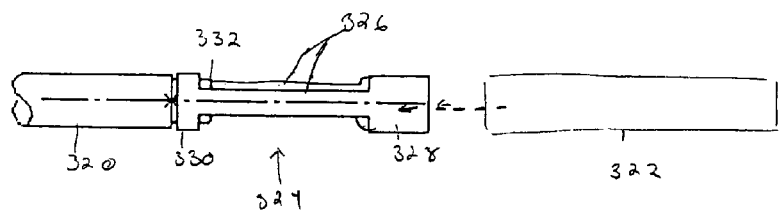
Figure 6C:
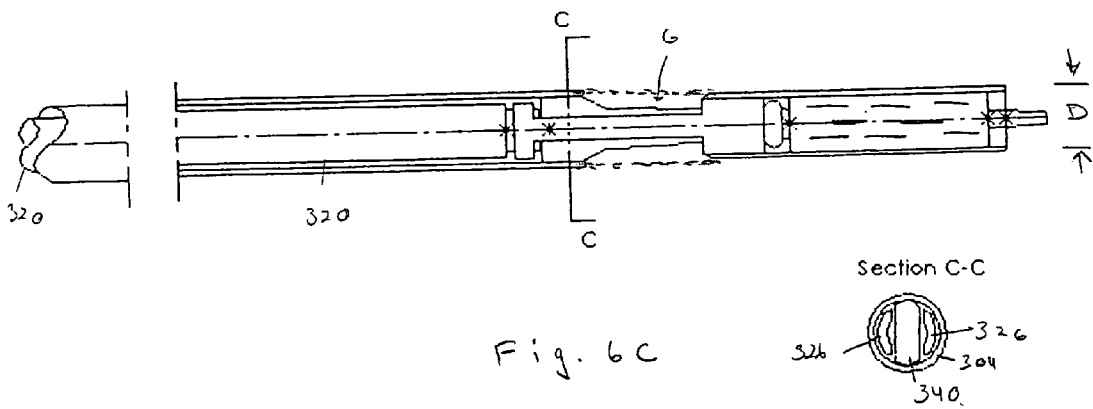

Another variation of the invention is shown in FIGS. 6A-6C. This is a two-sided device. By two-sided, what is meant is that two bridge sections 326 are provided in the connector 324 or otherwise. To accommodate these members, the connection is provided by a spanning or web member 340. It can be press-fit or otherwise attached or connected to opposing wall portions 342 of sleeve 304. Thus assembled, two pass-throughs are provided, one for each bridge section crossing over into the core wire lumen of the device. Section C-C in FIG. 6C provides a view of the components so-arranged.

Yet, except for the symmetry that such an approach provides over that of the one-sided approach (and concomitant advantages in terms of consistency in flexibility and distribution of loads, for example), the system is much like that shown in FIGS. 5A-5C. Accordingly, for the sake of brevity further discussion is omitted. Still, it is noted that advantages of a two-sided system over a one-sided system in terms of dynamic performance may prove to be important—especially in more demanding applications of the delivery device where a one-sided system might be more prone to kinking or biased behavior.

Figure 7:
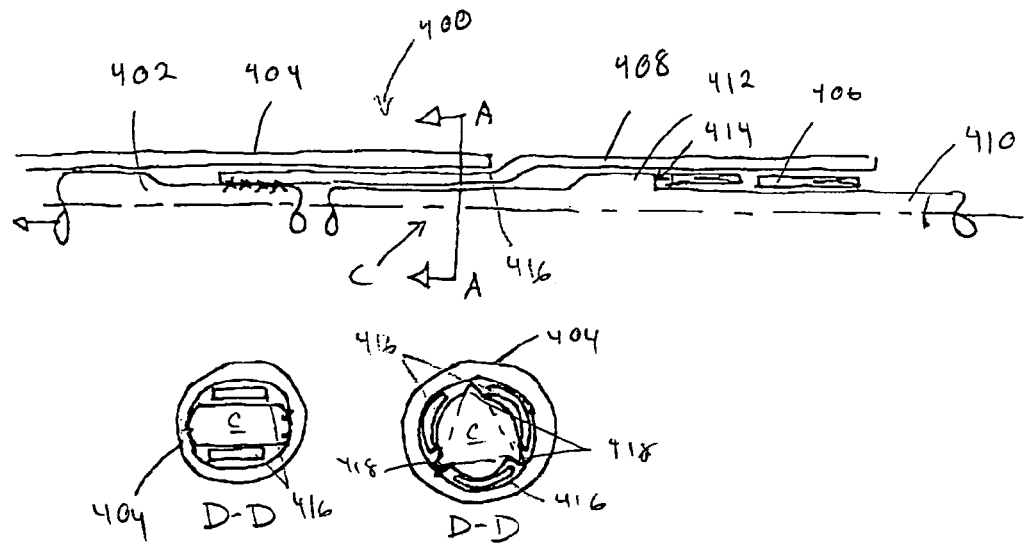
FIG. 7 provides detailed views of an alternative restraint approach that may be employed in the present invention.

FIG. 7 shows further optional aspects of the invention. Specifically, it illustrates a diameter-adaptive restraint as discussed above. Alternate sections A-A picture two-sided and three-sided connection approaches in line with those discussed above. Regarding the three-sided approach, this will offer a further improved quality of balanced performance.

In any case, the side sectional view in FIG. 7 show a distal portion 400 of delivery device 200. For ease of illustration, only half of the structure is shown. In this view, corewire 402 is slidingly received by a sleeve 404. A stent 406 is held in a collapsed configuration by a restraint 408 over an extension wire/member 410 connected to sleeve 404. A shoulder section 412 is provided on the extension. A distal surface 414 defined by the shoulder provides a stent abutment feature.

Connection options between the extension member and the sleeve are shown in sections D-D. The sections show the connection sections "C" as well as the manner in which bridge sections 416 pass by the same.

Note, further that the restraint in this variation of the delivery device may change diameter from a diameter external to the stent to a diameter internal to the delivery device. Yet, this need not be the case. However, it provides a highly space-efficient system, in which the length of the restraint and any bridge sections can be minimized.

Furthermore, it should be noted that the device may be configured such that bridge sections are progressively formed by cutting the restraint apart as it is drawn into the sleeve. Blade or wedge portion 418 can assist in such action. Alternatively, the restraint may be scored, perforated or otherwise made splittable so that simply being pulled into openings across the connection C separates the restraint into bridge sections.

Figure 8A:
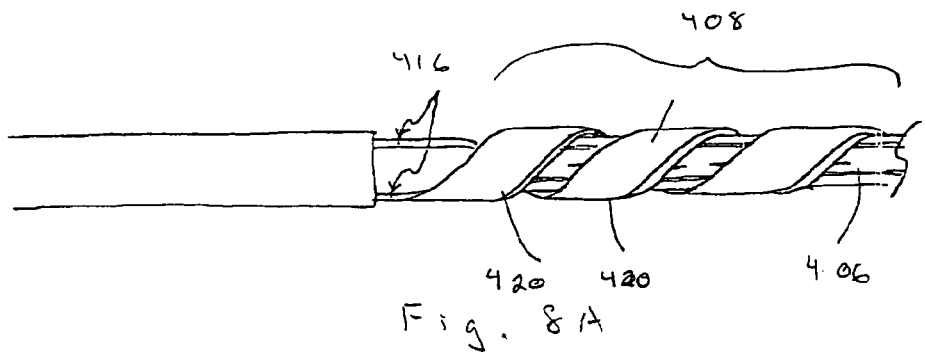
FIG. 8A is a side view of yet another restraint approach as may be employed in the invention.
Figure 8B:
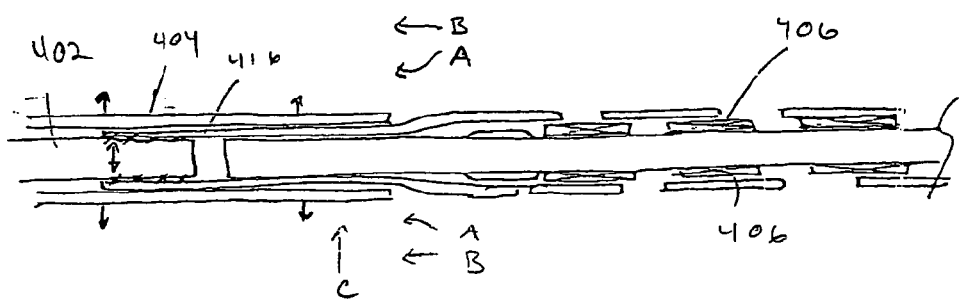
FIG. 8B is a side-sectional view of the structure shown in FIG. 8A.

Still further, it is contemplated that the restraint may be pre-split. An example of such a case is shown in FIGS. 8A and 8B. Here, restraint portion 500 comprises a plurality of bands or ribbons wound about the stent. Bridge sections 416 adjoin the restraint portion(s). The manner in which each band 420 wraps around and holds the stent 406 in a collapsed profile is best illustrated in FIG. 8A.

FIG. 8B shows the manner in which the band/straps 420 may be configured as a diameter adaptive restraint. In this regard, a section will pass under and into sleeve past its connection with extension wire 410 (again, optionally terminating in an atraumatic tip). Path "A" diagrammatically illustrates this action. Alternatively, at least the sleeve 404, but likely also the core member 402 can be expanded as indicated, such that the restraint slides directly into the same. Yet another option to facilitate the action indicated by path B is to provide a sleeve with a reduced wall thickness extension (such as in the form of thin-walled polymeric tubing) or by providing hypotubing with a thinned down distal end—such as by swaging, grinding or another manufacturing technique.

Figure 9:
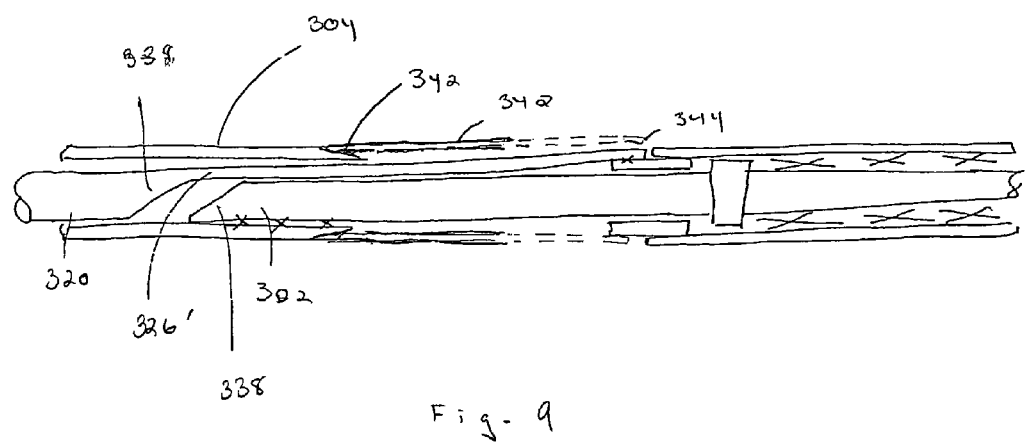
FIG. 9 is a side view of a variation of the invention related to that shown in FIGS. 5A-5C.

FIG. 9 shows a variation of the invention related to that shown in FIG. 5C. This variation of the invention employs an extension from the core wire as a bridge section 326'. Both of the extension member 302 and core wire may be undercut or tapered as in complimentary sections 328 (or otherwise) to facilitate uniform flexibility and/or reduce system stress-raisers. In addition, sleeve 304 includes an extension 342 thereto connected at another tapered section 340. The length of this taper (as with any other shown) may be varied, for example, to provide a uniform performance transition between members. Extension 342 is advantageously made of a lower modulus and/or thinner material than sleeve 304 (such as plastic vs. metal) to promote flexibility of the distal end of the device. As with the sleeve itself, the length or terminal placement of the sleeve extension 344 may be varied as indicated by the broken/phantom line.

Figure 10:
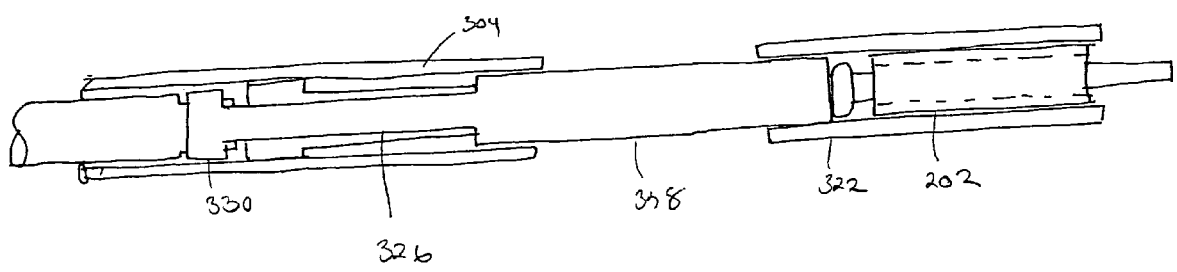
FIG. 10 is a side view of a variation of the invention related to that shown in FIGS. 6A-6C.

FIG. 10 shows a variation of the optional configuration noted with respect to FIG. 6C above. More specifically, sleeve 304 extends over bridge sections 326. In addition connector section 328 is lengthened. Such a configuration may be desired in order to provide an overall longer or more flexible distal end.

FIGS. 11A and 11B are cross-sectional side views of distal portions of another variation of the present invention. In FIG. 11A, a more proximal portion of the distal end of the device is shown. This variation, closely resembles the variation in FIG. 9 except for that it includes a coil 350 surrounding both the bridge segment/core wire extension 326' and extension member 302. The coil may be ribbon wound in a helical fashion, tubing laser or EDM cut into a spiral, round wire, etc. Such a form-factor advantageously decreases profile. Still, the coil may comprise round or square wire wound into a coil. The coil will generally be metallic (e.g., stainless steel, titanium alloy, NiTi, platinum, etc.). At smaller sizes, metal may be required to offer sufficient resistance from cutting by bridge member 326' and to secure it from separating from extension wire 302 when actuated along a tight curve.

An important aspect of the invention that is well illustrated in FIG. 11A is the manner in which bridge segment 326' parallels extension member 302 in order to conserve space. This arrangement offers particular elegance in component size miniaturization. Manufacturability is also benefited in that sleeve 304 is quite open across from the connection between extension member 302 and sleeve 304 prior to insertion of the core wire 320 during assembly. This approach (indicated by the double arrow) allow for relative ease of access for soldering or otherwise connecting the pieces.

The coil may be secured at a proximal point or location "PC" to the extension member or sleeve. Then, by preloading the structure and securing it at a distal location "DC" to the restraint (optionally, by way of an intermediate band 328 shown in FIG. 11B) the system is preloaded to help in withdrawing the restraint from the stent when desired. In this manner, the coil may serve two purposes. For the preload application, it may be desirable to make the coil of a highly elastic or high strength material such as NiTi or Stainless Steel. However, other connection schemes are possible.

Figure 12A:
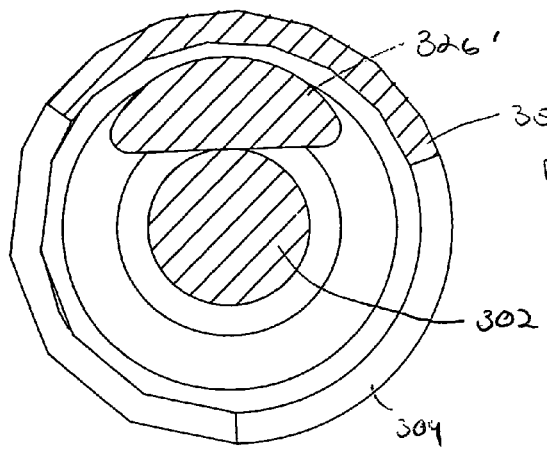
FIGS. 12A-12C are cross-sectional views of the variation of the invention shown in FIGS. 11A and 11B, taken along lines C-C, D-D and E-E, respectively.
Figure 12B:
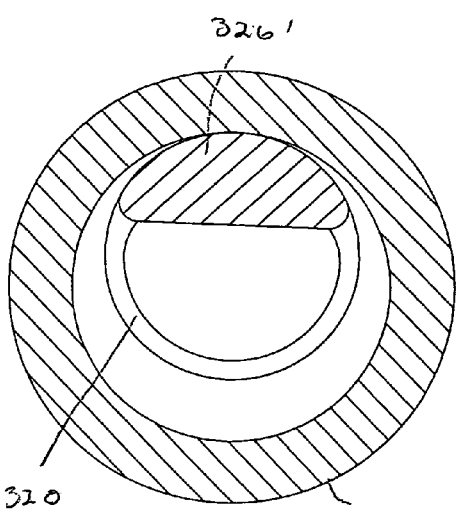
Figure 12C:
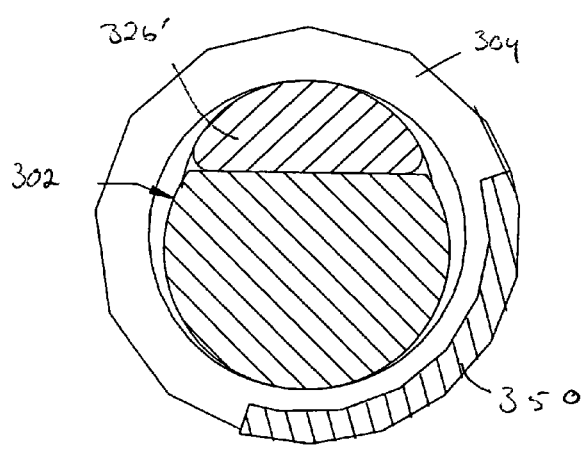

FIG. 11B also shows an optional stent blocker/marker 306, restraint 322 and stent 202 within a receiving zone over extension member 302. Additional moving markers may be provided, though none are shown. FIGS. 12A-12C are cross-sectional views of the variation of the invention shown in FIGS. 11A and 11B, taken along lines C-C, D-D and E-E, respectively. They the various components noted in the previous figures. In addition, they help illustrate the relative sizing of the parts as may be useful in optimizing system performance, particularly the manner in which bridge segment 326' is flattened or coined relative to the main core wire body 320. Also worth noting is that each of the components fit within the same envelope. In other words, the coil member can be added to the system without increasing its overall diameter.

FIG. 13 is a cross-sectional side view of another variation of the present invention. As shown, the distal end 300 of the system is on the left. Again, various ones of the parts resemble those above. The greatest difference between the systems is observed in connection with the bridge member 326". Here, the member is a hollow member shown in the form of a slotted tube. Slot 360 allows bridge tube to slide past the connection between the connection between extension member 302 and sleeve 304.

The sleeve optionally extends beyond this connection point "C" as shown. Such an approach offers a system less prone to contamination and potentially more stable in actuation. However, it may require a weld-type joint or an interlocking interface with a hole (not show) in sleeve. As above, cross-sectional views taken along various lines—in this case FIGS. 14A-14C taken along lines B-B, C-C and D-D, respectively—illustrate optional relationships between the constituent parts of this variation of the invention.

Figure 15:
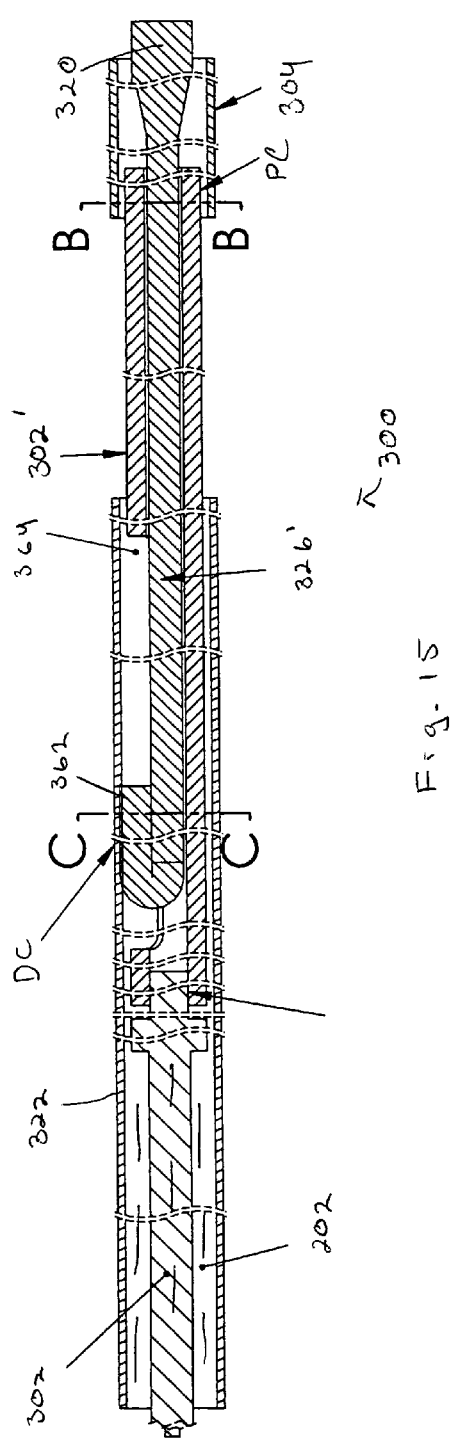
FIG. 15 is a cross-sectional side view of still another variation of the invention.

FIG. 15 is a cross-sectional side view of a distal end 300 of still another variation of the invention. As above, FIGS. 16A and 16B provide cross-sectional views at various points along the distal end 300 of the device, taken along lines B-B and C-C, respectively.

Figure 16B:
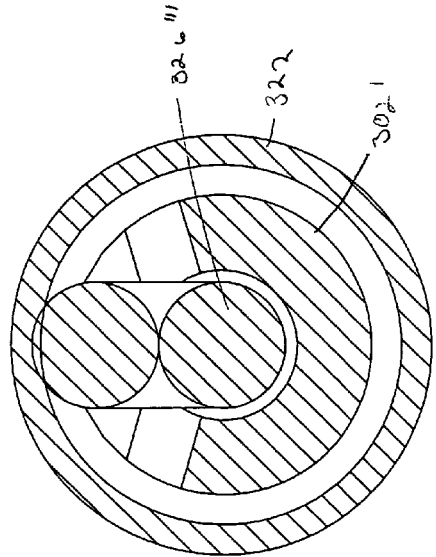
FIGS. 16A and 16B are cross-sectional views of the variation of the invention shown in FIG. 15, taken along lines B-B and C-C, respectively.
Figure 16A:
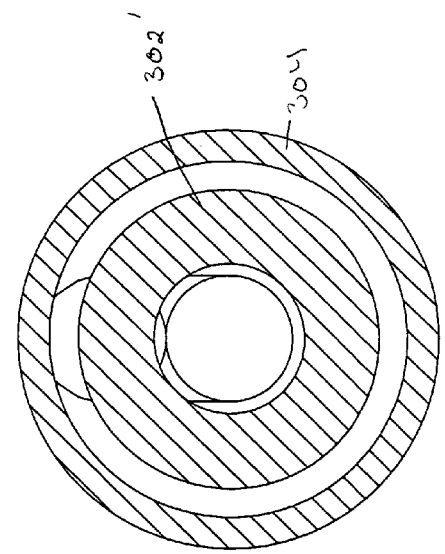

In the variation of the invention in FIGS. 15, 16A and 16B, the extension member comprises a wire section 302 upon which stent 202 is mounted, along with a tubular proximal section 302'. The tubular proximal sections surround bridge segment 326' extending from core wire and crossing over to make a distal connection "DC" with restraint 322 by way of optional turn 364. The bent or turned-back section 362 offers a convenient means of spanning the space between the internally actuated core member 320 and the exterior restraint 322. A proximal connection "PC" may be a solder joint, a glue joint, a weld joint as may be the distal connection. In addition, the proximal connection may be an interference fit—or be avoided altogether by integrating the function of the proximal extension member into sleeve 304, by extending the sleeve and making a slot therein to allow traversal of turn 362 or another cross-over structure therethrough.

Extension member 302' is shown as a tube with a slot 364 formed therein. The slot is shown covered by restraint 322, though this need not be the case. Indeed, this "tube" 302' and tube 326" may be configured otherwise. Either entity may be any sort of body including various oval, hex, square, etc. sections—either with a closed periphery at some location or slotted aling the entire length so as to define one-half, two-thirds of a tube or any of a C, U, V section. etc.

Regardless of all such optional constructions or alternative variations, in a generic sense, the delivery guide member body comprises or consists substantially of an inner member (possibly a core member in order to minimize size and maximize strength) set within a proximal tubular member or sleeve, with an extension member secured to or within the tubular member. The extension section carries the stent and preferably terminates in an atraumatic tip. A restraint is provided external to a collapsed stent, the restraint being actuated by the core member in an inside-out fashion, particularly by way of a bridging connection between the inner member and the restraint.

In regard to any such system, it is to be understood that conventional materials and techniques may be employed in the system construction. In this regard, it will often be desired to provide a lubricious coating or cover between moving components to reduce internal system friction.

In addition, it is to be understood that various radiopaque markers or features may be employed in the system to 1) locate stent position and length, 2) indicate device actuation and stent delivery and/or 3) locate the distal end of the delivery guide. As such, various platinum (or other radiopaque material) bands or other markers (such as tantalum plugs) may be variously incorporated into the system. Alternatively, or additionally, the stent stop or blocker member may be made of radiopaque material. Especially where the stent employed may shorten somewhat upon deployment, it may also be desired to align radiopaque features with the expected location (relative to the body of the guide member) of the stent upon deployment. For example, it may be desired to incorporate radiopaque features into the restraint and/or bridge or connector sections so that the deployment motion of the device is visible under fluoroscopy. Exemplary markers that may be of use are shown at a proximal end of the stent in FIG. 4 as elements A and A'—on the delivery guide body and restraint, respectively—and at a distal end of the stent on the restraint as element B.

Though the invention has been described in reference to several examples, optionally incorporating various features, the invention is not to be limited to that which is described or indicated as contemplated with respect to each embodiment or variation of the invention. The breadth of the present invention is to be limited only by the literal or equitable scope of the following claims. That being said,

We claim:

1. A stent delivery system comprising:
   a self-expanding stent;
   an inner wire;
   an outer sleeve, the inner wire slidingly received within the sleeve;
   an extension member having a proximal end attached to a distal portion of the outer sleeve;
   a restraint holding the stent collapsed over a distal wire portion of the extension member; and
   a bridge segment connecting a proximal end of the restraint to a distal end of the inner wire so that proximal retraction of the inner wire relative to the outer sleeve retracts the restraint to release the stent.

2. The system of claim 1, wherein the inner wire comprises a corewire.

3. The system of claim 1, wherein a proximal portion of the delivery guide consists essentially of the sleeve and the inner wire, wherein the inner wire is a core wire.

4. The system of claim 1, wherein the bridge segment is an integral extension of the inner wire.

5. The system of claim 1, wherein the bridge segment comprises a member attached to the inner wire.

6. The system of claim 1, wherein the bridge segment has a flattened shape.

7. The system of claim 1, wherein the extension member consists essentially of a wire.

8. The system of claim 1, further comprising a coil surrounding at least a portion of each of the extension member and the bridge segment.

9. The system of claim 8, wherein the coil is secured to each of the sleeve and restraint.

10. The system of claim 1, wherein the extension member comprises a hollow body proximal to the distal wire portion of the extension member.

11. The system of claim 10, wherein the hollow body comprises a tube.

12. The system of claim 11, wherein the tube is slotted at a distal end.

13. The system of claim 1, wherein the connection between the extension member and the sleeve is proximal to a distal end of the sleeve.

14. The system of claim 1 or 13, wherein the sleeve overlays the bridge segment.

15. The system of claim 1, wherein the bridge segment comprises a hollow body.

16. The system of claim 15, wherein the hollow body comprises a tube.

17. The system of claim 1, wherein only one bridge segment is provided.

18. The system of claim 1, wherein a plurality of bridge segments are provided.

19. The system of claim 1, wherein a stent stop surface is provided to abut a proximal end of the stent.

20. The system of claim 1, wherein the connection between the extension wire and the sleeve is symmetrical about an axis along the tubular body.

21. The system of claim 1, 3, or 8, wherein the system comprises an atraumatic tip.

* * * * *